(12) United States Patent
Capik

(10) Patent No.: US 9,734,292 B2
(45) Date of Patent: Aug. 15, 2017

(54) APPARATUS, SYSTEM, AND METHOD FOR THERAPY BASED SPEECH ENHANCEMENT AND BRAIN RECONFIGURATION

(71) Applicant: Neurodar, LLC, Redding, CA (US)

(72) Inventor: John Capik, Redding, CA (US)

(73) Assignee: Neurodar, LLC, Redding, CA (US)

( * ) Notice: Subject to any disclaimer, the term of this patent is extended or adjusted under 35 U.S.C. 154(b) by 233 days.

(21) Appl. No.: 13/710,378

(22) Filed: Dec. 10, 2012

(65) Prior Publication Data

US 2013/0231942 A1   Sep. 5, 2013

Related U.S. Application Data

(60) Provisional application No. 61/568,406, filed on Dec. 8, 2011.

(51) Int. Cl.
*G06F 19/00* (2011.01)
*G09B 5/06* (2006.01)

(52) U.S. Cl.
CPC .......... *G06F 19/34* (2013.01); *G06F 19/3481* (2013.01); *G09B 5/06* (2013.01)

(58) Field of Classification Search
CPC .................... G06Q 50/22; G06Q 50/24; G06F 19/322–19/327
See application file for complete search history.

(56) References Cited

U.S. PATENT DOCUMENTS

| 4,020,567 | A | 5/1977 | Webster |
| 4,615,680 | A | 10/1986 | Tomatis |
| 5,940,798 | A | 8/1999 | Houde |
| 2002/0032583 | A1* | 3/2002 | Joao ................................. 705/2 |
| 2004/0194610 | A1 | 10/2004 | Davis |
| 2007/0112585 | A1* | 5/2007 | Breiter .................... G06F 19/12 705/2 |
| 2009/0258333 | A1* | 10/2009 | Yu ................................. 434/157 |

(Continued)

FOREIGN PATENT DOCUMENTS

GB          2458461 A      9/2009

OTHER PUBLICATIONS

PCT/US2012/068828 International Search Report and Written Opinion, Mar. 28, 2013, Korean Intellectual Property.

(Continued)

*Primary Examiner* — Sean K Hunter
(74) *Attorney, Agent, or Firm* — Kunzler Law Group

(57) ABSTRACT

An analysis request module provides to a human subject an action request for imitation. A data collection and deconstruction module digitally collects action request response data from a human subject and deconstructs the data into subcomponents. The analysis module compares the subcomponents of the response data with the matching subcomponents of the action request and correlates the subcomponents of the physiological response with at least one of the subcomponents of the subject's response to the action request and a baseline state. An intelligent processing module receives physiological subcomponent input and response data input and dynamically associates the physiological subcomponents and other data subcomponents and recommends a new action configured to move the subject response toward a more accurate imitation of the action request.

29 Claims, 28 Drawing Sheets

(56) References Cited

U.S. PATENT DOCUMENTS

2010/0062403 A1    3/2010  Williams et al.

OTHER PUBLICATIONS

National Institutes for Health (NINDS Aphasia Information page: NINDS, 2008.
Andrea Norton, Lauryn Zipse, Sarah Marchina, and Gottfried Schlaug. "Melodic Intonation Therapy", The Neurosciences and Music III: Disorders and Plasticity, 2009.
MIT Melodic Intonation Therapy Kit, www.proedinc.com/customer/Productview, known about as early as Dec. 2011.

* cited by examiner

1512

1511 —
```
1. RULE: ASK_FOR_PATIENT_RESPONSE
2. {
3.    STATE:
4.        SystemState == DASR_Happy_Birthday
5.    PRIORITY:
6.        priority == 1;
7.    CHECK:
8.        isRecognizerLoaded == TRUE;
9.        isRecognizerOnline == TRUE;
10.       isMicActive == TRUE;
11.       isPatientLeftMotionSensor Online == TRUE;
12.       isPatientRight MotionSensor Online == TRUE;
13.       isPatientAudioHeadSetOnline == TRUE;
14.       isTherapistLeftMotionSensor Online == TRUE;
15.       isTherapistMotionSensor Online == TRUE;
16.       isTherapistAudioHeadSetOnline == TRUE;
17.       isPatientSessionActive == TRUE;
18.   ACTION:
19.       playLeftRightEarRequest("Please Say Happy Birthday")
20.       havePatientResponse = FALSE;
21.       RULE(ACTIVATE_SPEECH_RECOGNITION));
22. }
```

1513 —
```
1. RULE: ACTIVATE_SPEECH_RECOGNITION
2. {
3.    STATE:
4.        SystemState == DASR_Happy_Birthday
5.    PRIORITY:
6.        priority == 1;
7.    CHECK:
8.        havePatientResponse == FALSE;
9.    ACTION:
10.       RecognizeAudioInput();
11.       SendMessage("Recognizing");
12.       RULE(GET_PATIENT_RESPONSE));
13. }
```

1514 —
```
1. RULE: GET_PATIENT_RESPONSE
2. {
3.    STATE:
4.        SystemState == DASR_Happy_Birthday
5.    PRIORITY:
6.        priority == 1;
7.    CHECK:
8.        havePatientResponse == TRUE;
9.    ACTION:
10.       DeconstructPatientResponse();
11.       havePatientResponse = FALSE;
```
1515 ——— `10.       RULE(ANALYSE_PATIENT_RESPONSE));`
```
11.       SendMessage("Have Patient Response [" + StrResponseStr + "]");
12. }
```

FIG. 15b

```
1. //One of the Conflict Rules
2. RULE: MULTIPLE_PATIENT_RESUEST_RULES
```

```
1. //One of the Conflict Rules
2. RULE: SPEECH_REC_RESULTS
```

```
1. //One of the Conflict Rules
2. RULE: SEND_PATIENT REQUEST
```

```
1.  //One of the Conflict Rules
2.  CONFLICT_RULE: ANALYSE_PATIENT_RESPONSE
3.  {
4.
5.  STATE:
6.      SystemState == DASR_HappyBirthday;
7.  PRIORITY:
8.      SystemPriority == 1;
9.      SessionPriority == CONFLICT;
10.
11. CHECK_CONFLICT:
12.     EEGInputData == TRUE;
13.     fMRIInputData == TRUE;
14.     leftGloveMotionSensorData == TRUE;
15.     rightGloveMotionSensorData == TRUE;
16.     speechRecInputData == TRUE;
17.     haveSpeechResponse == TRUE;
18.     haveLeftMotionSensorResponse == TRUE;
19.     haveRightMotionSensorResponse -- TRUE;
20.     haveEEGData == TRUE;
21.     havefMRIData == TRUE
22.     haveSpeechRecData == TRUE;
22. ACTION:
23.     if(haveLeftMotionSensorResponse == TRUE)
24.     {
25.         RULE(EVALUATE_ALL_PATIENT_DATA);
26.     } else {
27.         RULE(REPEAT_PATIENT_REQUEST);
28.     }
29.     recognizerParmAcousticModel = "AcousticModelAphasia1";
30. }
```

FIG. 15c

APPARATUS, SYSTEM, AND METHOD FOR THERAPY BASED SPEECH ENHANCEMENT AND BRAIN RECONFIGURATION

CROSS-REFERENCES TO RELATED APPLICATIONS

This application claims the benefit of U.S. Provisional Patent Application No. 61/568,406 entitled "A Software System that Provides Automated Intelligent Testing, Diagnosing, Therapy and Training for Subjects with Aphasia" and filed on Dec. 8, 2011, for John Capik, which is incorporated herein by reference.

BACKGROUND

Field

This invention relates to speech enhancement and more particularly relates to speech therapy and associated brain reconfiguration for subjects suffering from brain-based speech deficiencies including aphasia.

Description of the Related Art

One in 272 Americans suffer from some form of aphasia. In non-fluent aphasia, also called expressive aphasia, subjects have difficulty in articulating, but in most cases there is relatively good auditory verbal comprehension. Examples of non-fluent aphasia are: Brocha's aphasia, Transcortical motor aphasia, and Global aphasia.

For years, it has been noted that there is a link between music and speech. Aphasic subjects have been capable of singing words that they cannot speak. In 1973, the first music-based treatment for aphasic subjects was introduced and titled Melodic Intonation Therapy or MIT.

MIT uses the musical element of speech (melody and rhythm) to improve expressive language by capitalizing on preserved function (singing) and engaging language-capable regions in the undamaged right hemisphere of the brain to compensate for the damage in the speech areas of the left hemisphere An aphasic subject may desire to repeat a requested phrase but cannot process the request using the left hemisphere of the brain because the speech areas are damaged. In some cases it has been shown that with proper therapy and retraining aphasic subjects can process the speech request through music by employing the right hemisphere of the brain.

The use of methods such as Melodic Intonation Therapy (MIT) is designed to lead a subject from singing to actually intoning or singing simple 2-3 syllable phrases to speaking more complex phrases across several different levels of complexity. A Session Guide may sing or hum the requests to the subject and may tap on the subjects hand in an effort to help advance the learning process when responding to speech requests. Some studies have suggested that tapping the left hand may engage a right-hemisphere sensorimotor network that controls both hand and mouth movements.

Effectiveness of these techniques is compromised, however, by factors including insufficient data from the subject, musical ability/inability of the therapist and its effect on the subject, inexactness in the coordination of tapping and singing due to human error and coordination from the therapist, inability to evaluate what approaches are more successful for each individual subject, lack of historical data from other prior subject sessions to guide the next step during the subject session, and human limitation on the therapist's ability to analyze a subject's response and formulate the most effective next step.

Thus, the current methodologies used to treat aphasic subjects fail to optimize the results and a need exists for a new technology to mitigate the current limitations of aphasia subject diagnosis, treatment and re-training.

SUMMARY

From the foregoing discussion, it should be apparent that a need exists for an apparatus, system, and method that provide greater precision and effectiveness in speech reconstruction therapy. Beneficially, such an apparatus, system, and method would overcome human error and limitations by supplementing the therapist's efforts with a powerful capability to analyze subject response and generate an effective new request.

The present invention has been developed in response to the present state of the art, and in particular, in response to the problems and needs in the art that have not yet been fully solved by currently available therapies. Accordingly, the present invention has been developed to provide an apparatus, system, and method for speech enhancement or reconstruction that overcome many or all of the current shortcomings in the art.

Provided herein is an apparatus for speech reconstruction or enhancement, brain reconfiguration, brain research, and brain damage diagnosis. The apparatus comprises an action request module configured to provide to a human subject an action request for imitation, wherein the action comprises producing speech, music, pitch, melody, rhythm, or another sound or action. The apparatus may further comprise a data collection module configured to digitally collect action request response data from a human subject. The data may comprise physiological data and action data or sound data comprising speech data, music data, rhythm data, or other sound data.

In various embodiments the apparatus as provided herein comprises a deconstruction module configured to deconstruct the data into subcomponents and an analysis module configured to compare the subcomponents of the response action data, speech data, music data, rhythm data, or other sound data with the matching subcomponents of the action request and to correlate the subcomponents of the physiological response with the subcomponents of the subject's response to the action request or a to baseline state.

The apparatus herein provided further comprises an intelligent processing module configured to receive physiological subcomponent input and action, speech, music, rhythm or other sound subcomponent input from the analysis module and to dynamically associate the physiological subcomponents and other data subcomponents and recommend a new action configured to move the subject response toward a more accurate imitation of the action request.

In certain embodiments of the apparatus, the data collection module, the deconstruction module, the analysis module, or the intelligent processing module operates in real time. In some embodiments either or both of the analysis module and the intelligent reasoning module is configured to apply machine logic and automated reasoning to the selection of the new action request The apparatus may further comprise a knowledge module comprising an active data module, an internal memory module, a memory storage module, a session memory module, a rules module a knowledge database or a rules database. In some embodiments the knowledge module is self-learning and configured to accrue and dynamically link stored or incoming data to analysis and/or decision making.

In some embodiments the apparatus provided further comprises a synchrotimer, a storage module, a process analyzer module, a data processing module, a data input capture module, a diagnostic module, a communication module, a testing module, a train module, a GUI, or a user interface module. The apparatus sometimes comprises a reconstruction module configured to reconstruct original sound, physiological or other data.

The intelligent processing module may further comprise an inferencing engine configured to implement the rules in the knowledge database according to specific conditions. The inferencing engine sometimes comprises an interpreter configured to execute chosen functions or actions based on the application of corresponding base rules, a scheduler configured to maintain control over system plans and functionality, or a conflict manager configured to maintain consistency of decisions according to rule priorities.

The session memory module may process and store data relating to a therapy, research or diagnostic session. In some embodiments the session memory module enables a session to be paused and resumed, either at the same location or at a different location.

In some embodiments the apparatus provided herein further comprises an import module configured to import external data. Physiological data may comprise heartbeat, respiration rate, or galvanic skin response. In certain embodiments the physiological data comprises neurological data, which may comprise at EEG, EGG, MRI, fMRI or DTI. The neurological data sometimes comprises indicia of elevated inter-hemispheric brain activity during action request response or the growth of the AF fiber.

Also provided herein is system for speech reconstruction or enhancement, brain reconfiguration, brain research, and brain damage diagnosis. The system comprises a therapeutic apparatus configured to supply a subject with an action to imitate. The action may comprise at least one of action, speech, music, rhythm, and other sound. The therapeutic apparatus is further configured to sense the subject's response, to deconstruct the response data into subcomponents, to compare the subject's response to the original action, and to supply a new action. The system further comprises a database configured to store a library of actions and subject responses and an incoming communication module configured to sense the subject's response and communicate the response to the therapeutic apparatus. The system may also comprise an outgoing communication module configured to communicate the new action to the subject, an input device; and an outside communication connection and an internal communication connection.

The system sometimes comprises a reconstruction module configured to reconstruct the deconstructed data. In some embodiments the system provided of further comprises an external data monitor. The external data monitor may be configured to measure at least one of heart rate, respiration rate, galvanic skin response, ECG, EGG, and MRI, fMRI and DTI. The system may comprise a communication protocol and an optional remote server platform.

In various embodiments the system provided herein comprises a computer program product comprising a computer readable storage medium storing a computer readable program code executed to perform operations for the therapeutic apparatus. The operations of the computer program product may comprise supplying to a subject an action to imitate, the action comprising at speech, singing, rhythm, or other sound, or action, sensing the subject response and deconstructing the response data into subcomponents. The computer program product may compare the subcomponents of the subject response to the subcomponents of the action request and correlate the subcomponents of the subject physiological response to the subcomponents of the previous response or to a baseline, and recommend a new action configured to bring the subject response closer to the action request. In certain embodiments the computer program product applies the data to an intelligent reasoning module configured to use acquired knowledge to formulate a next action request.

Further provided herein is a method for promoting at least one of speech reconstruction or enhancement, brain reconfiguration, brain research and brain damage diagnosis. The method comprises supplying to a subject an apparatus configured to provide the subject with an action request comprising speech, music, rhythm, other sound or action. The apparatus is configured to sense the subject response, to compare the subject response to the original action, and to supply a new action. The method further comprises measuring the subject's physiological response to the action and moderating the new action to optimize the physiological response.

The method may further comprise supplying an external data monitor. In certain embodiments the external data monitor is configured to measure at least one of heart rate, respiration rate, galvanic skin response, ECG, EGG, and DTI. The physiological response sometimes comprises a brain wave, AF fiber growth, brain reconfiguration, or other neurological changes.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 15b is a schematic block diagram illustrating one embodiment of rules that might represent part of the rule set for controlling a subject session with a session guide;

FIG. 15c is a schematic block diagram illustrating one embodiment of a rules conflict resolution module in accordance with the present invention;

DETAILED DESCRIPTION

Figure 1:
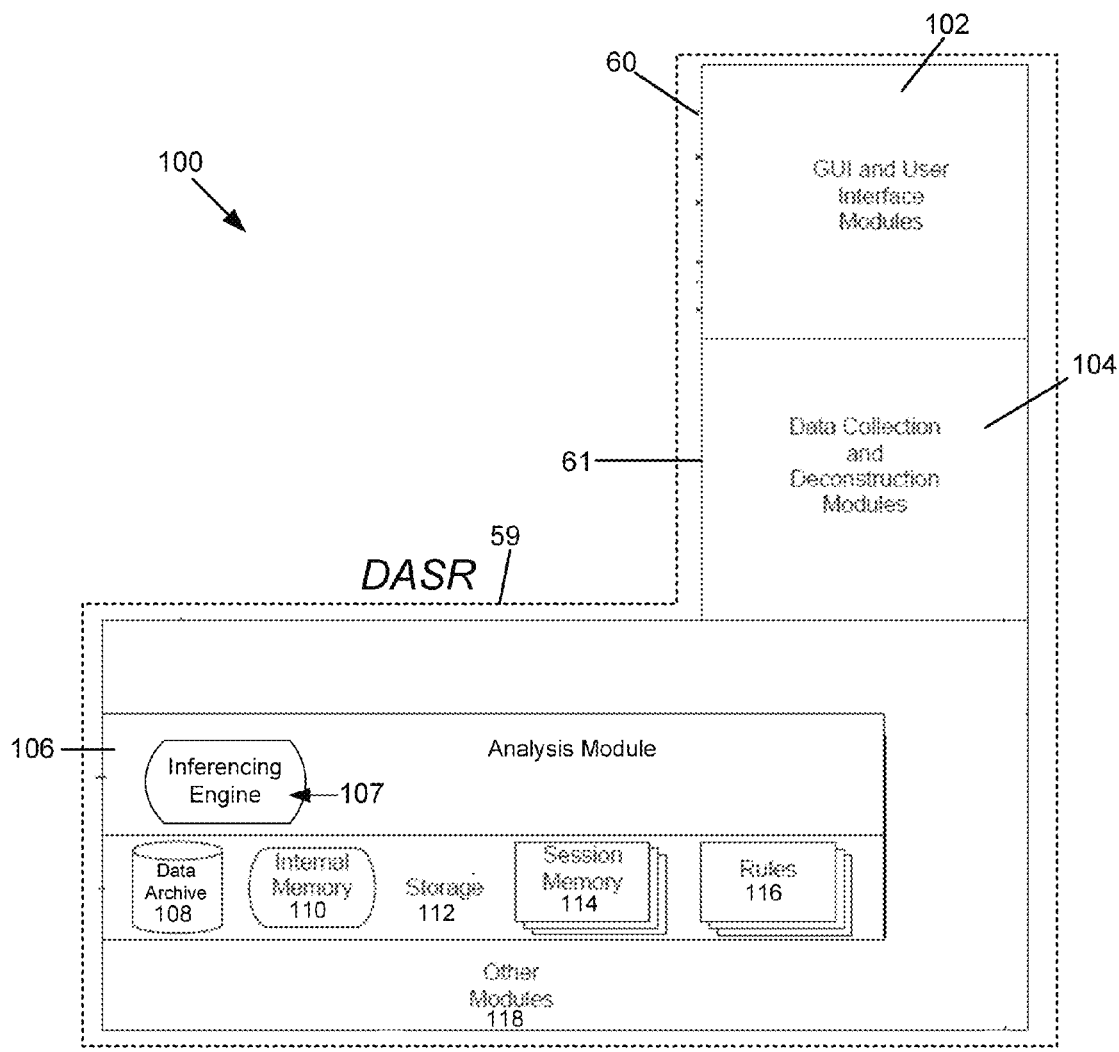
FIG. 1 is a schematic block diagram depicting one embodiment of an apparatus for speech reconstruction or enhancement, brain reconfiguration, brain research, and brain damage diagnosis in accordance with the present invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The apparatus, system, and method as provided herein relate to dynamic, adaptive, speech reconstruction or enhancement and brain reconstruction, brain research, and brain damage diagnosis, including without limitation the testing, diagnosing and training of subjects with aphasia and other trainable brain injuries. As herein provided, aphasia subjects exhibiting non-fluent aphasia can be assisted in recruiting undamaged portions of the brain to compensate for the damaged left hemisphere speech centers. In certain embodiments the therapy measurably promotes reconfiguration of the damaged brain through use of a monitored subject-system feedback loop using speech, music, and rhythm.

FIG. 1 is a schematic block diagram depicting one embodiment of an apparatus 100 for speech reconstruction or enhancement, brain reconfiguration, brain research, and brain damage diagnosis in accordance with the present invention. As depicted, the apparatus 100 comprises a graphical user interface (GUI) 102, a data collection and deconstruction module 104, an analysis module 106, an inferencing engine 107, and a storage module 112. In some embodiments the storage module 112 comprises a data archive 108, an internal memory module 110, a session memory module 114 and a rules module 116.

The analysis module 106 may be configured to receive input from the other modules and formulate an action request for a therapy, research, or diagnostic subject. The action may comprise producing speech, music, pitch, melody, rhythm, or another sound or action. The analysis module 106 may be any type of intelligent-based design known in the art, including without limitation a neural net design and a forward/backward chaining inference engine expert rule-based system. It is understood that other architectural designs can be used to achieve the same result.

In some embodiments the GUI captures, and the data collection and deconstruction module 104 deconstructs, various amounts of data in real-time or in background mode about the subject and his responses to therapy requests. In certain embodiments the patient response data comprises speech data, music data, rhythm data or action data. The action data may comprise rhythmic tapping, hand motion, body motion, head motion, facial motion or other type of physical action. The patient response data sometimes comprises physiological data and may comprise neurological data. In certain embodiments the inferencing engine 107 uses the deconstructed data along with data and results acquired and stored from prior subject sessions in the data archive 108. Various modules, sometimes comprising the analysis module 106, receive the deconstructed data which they analyze, correlate, weight and prioritize. The analysis module 106 may be configured to compare the subcomponents of the response action data, speech data, music data, rhythm data, or other sound data with the matching subcomponents of the action request and to correlate the subcomponents of the physiological response with the subcomponents of the subject's response to the action request or a to baseline state.

The analysis module 106 that draws on expert knowledge including that stored in the memory storage module 112, sometimes comprising the internal memory module 110, the session memory module 114 and the rules module 116. The analysis module 106 may use this knowledge to make intelligent real-time decisions on how to proceed with each component of a subject/Session Guide session. In certain embodiments the other modules 118 may comprise additional existing modules as well as new modules added to meet need or technological changes and advances.

Figure 2:
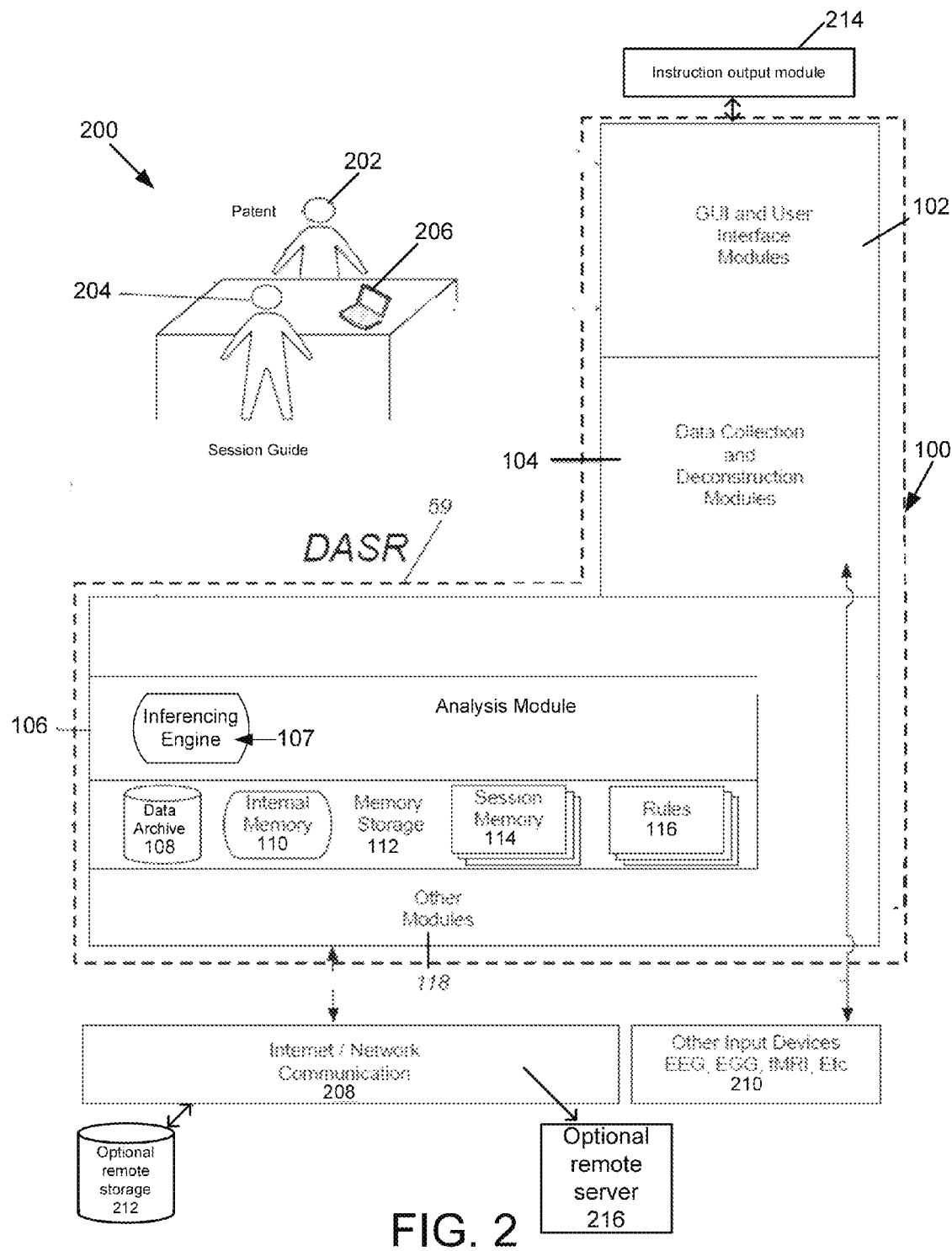
FIG. 2 is a schematic block diagram depicting one embodiment of a system for speech reconstruction or enhancement, brain reconfiguration, brain research, and brain damage diagnosis in a therapeutic setting in accordance with the present invention.

FIG. 2 is a schematic block diagram illustrating one embodiment of a system 200 for speech reconstruction or enhancement, brain reconfiguration, brain research, and brain damage diagnosis in a therapeutic setting in accordance with the present invention. As depicted, the system 200 comprises the apparatus 100 as shown in FIG. 1, a subject 202, a session guide 204, one or more data input devices 206, an optional internet/network communication channel 208, other input device 210, an optional remote storage 212, an instruction output module 214, and an optional remote server 216. In some embodiments the session guide 204 is a therapist. In various embodiments the session guide 204 is a researcher, technologist, integral system guide, artificial intelligence, or other entity. In certain embodiments the session guide 204 prompts the apparatus 100 to deliver an instruction to the subject 202 via the instruction output module 214. In other embodiments the system itself automatically prompts the apparatus 100 to deliver an instruction to the subject 202 via the instruction output module 214. In other embodiments the system itself automatically prompts the Session Guide with one or more choices that the session guide can then select from to prompts the apparatus 100 to deliver an instruction to the subject 202 via the instruction output module 214. The instruction may include speech, music, or rhythm or other responses for the subject to reproduce or physical (i.e. touch, vibration, sensation etc.). The subject 202 responds to the data input device 206 which communicates the response to the apparatus 100 sometimes via the internet network communication channel 208 and sometimes directly to the apparatus 100 without an internet network connection. In certain embodiments the other input device 210 comprises an electroencephalogram (EEG), a heart rate monitor, an electrocardiogram (EKG) a respiration rate monitor, a galvanic skin response monitor, a functional magnetic resonance image (fMRI), a magnetic resonance image (MRI), a diffusion tensor image (DTI) or an electroglottal graph (EEG). The other input device 210 may operate in real-time or may comprise a delayed measurement. In certain embodiments the system 200 imports external data that is not capable of being directly captured in real-time, including due to restrictions on the external device capturing the data. In some embodiments the imported data is correlated with the subject session and samples along with the other real-time data performed so that said external data may be available for post-session analysis and research and development purposes.

The system 200 or the session guide 204 may first make a request of the subject 202 through some sort of audible or visual command. The subject 202 then responds to the request. In certain embodiments the patient response comprises speech, music, rhythm, or action. The action may comprise rhythmic tapping, hand motion, body motion, head motion, facial motion or other type of physical action. The patient response sometimes comprises a physiological reaction including without limitation heart rate, respiration rate, galvanic skin response and neurological response. In some embodiments the system 200 collects and consumes all data in real-time and deconstructs the data. In certain embodiments the intelligent reasoning and inference module 106 uses the data in real-time to make decisions on how to proceed in the next phase of the session. Based on the subject 202's response to the prior session requests, the system 200 uses the current data collected from the subject 200 and also uses prior data and knowledge about prior sessions from other subjects and makes an intelligent decision made by the analysis module 106 to generate a request to present to the subject 202 to effectively elicit the desired subject response.

System 200 provided herein collects data in an amount that may exceed the real-time capture capacity of the human mind. The system 200's capability to intelligently process all data may also exceed the capacity of the human mind and Session Guide. All data is deconstructed into it simplest forms and components for current and future evaluation and correlation and can be quickly accessed by the system 200 as necessity dictates.

In some embodiments the system 200 relates to a dynamic adaptive speech reconstruction (DASR) process. The system 200 sometimes comprises optional remote storage 212. The optional remote storage 212 may comprise a larger DASR technology storage unit (Remote System). In either remote or local configuration the system 200 has the capacity to record sounds specifically from a human voice with a microphone or other device as well as play back audio through the instruction output module 214. The instruction output module 214 may comprise without limitation audio speakers or headphones. Audio output may be speech, musical promptings or other types of promptings such as an action, beat or a tapping sound or other sound. The type of audio played back is open ended and can comprise whatever the system requires in order to elicit the proper response from the subject.

The precise output of the system 200 obviates the necessity for the Session Guide 204 to generate the audio output (i.e. the Session Guide speaking or singing) and thus eliminates variables introduced by human error, which might confuse the subject 202 or interfere with response and learning. For example, the Session Guide 204 might sing slightly off pitch or be out of beat with the music or the tapping on the subject 202's hand. In another example, the sound of the Session Guide 204's voice may not be pleasing to the subject 202, may remind the subject 202 of someone who caused stress in the subject 202's life or may elicit other negative subject 202 feelings.

In some embodiments the input device 210 reads subject 202 physiological responses including without limitation heartbeat, respiration rate, or galvanic skin response, allowing the apparatus 100 to evaluate stress at the delivery of a specific voice type. If certain indicators in data tell the system 200 that there is an increase in stress when a specific voice is used, the system 200 may switch to another voice through an intelligent real-time decision and then measure the subject 202 data again for a decrease in stress. This adjustment may have a major impact on the subject 202/Session Guide 204 session, allowing the subject 202 to be comfortable and concentrate on the session itself and the session requests. Access to data about the subject 202 and optionally prior subjects, may eliminate guesswork and deliver interactive sessions that are precisely and intelligently focused on the unique needs and recovery of each individual subject 202.

The system 200 may be interfaced with any device known in the art to collect data about a subject 202, including without limitation by adding modules 118 to the apparatus 100, and is also by way of software design and new modules 118 capable of interfacing with new devices in the future. It is understood that the system 200 provided herein is not limited to any specific software or hardware architecture design.

In certain embodiments the various modules of the system 200 incorporate melodic intonation therapy (MIT) rules and may incorporate additional data and intelligent processing and reasoning capabilities as well as data from prior sessions with other subjects. The system 200 may further comprise a Session Guide 204 screen and keyboard or mouse or similar GUI input device an optional remote DASR server 216 and additional knowledge and data accessed remotely via Internet/Network or similar connection 208. Some embodiments may comprise noise canceling microphone headsets and other wearable input/output devices. In various embodiments the system 200 further comprises software and hardware for various modules that can be added or removed at will. The Session Guide 204 may have a video display screen with a GUI displayed from the system 200. In certain embodiments the subject has a video display screen that is used by the system 200 to display relevant subject 202 data and requests visually when appropriate.

Figure 3A:
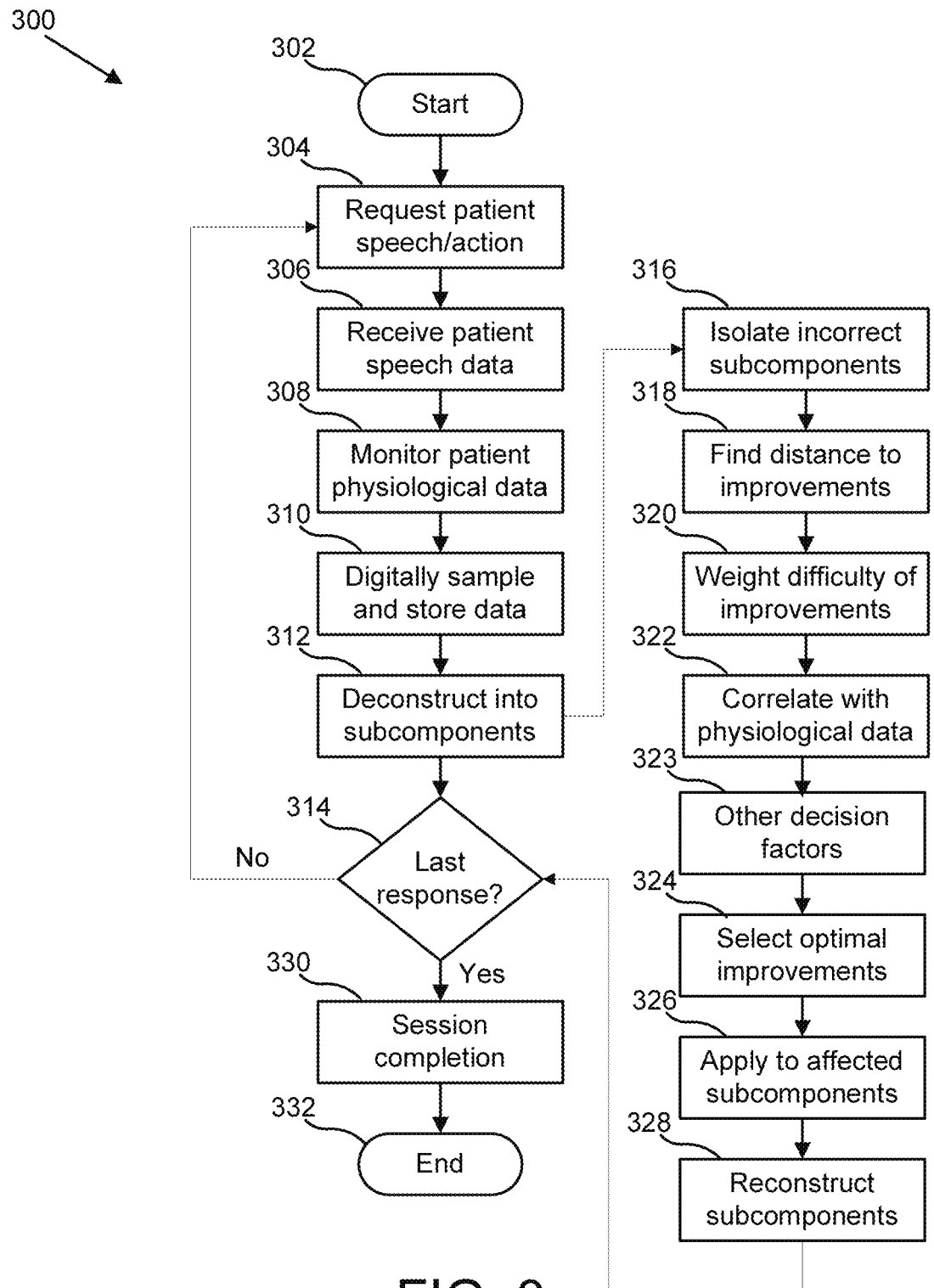
FIG. 3a is a schematic flow chart diagram depicting one embodiment of a method for speech reconstruction or enhancement, brain reconfiguration, brain research, and brain damage diagnosis in accordance with the present invention.

FIG. 3a is a schematic flow chart diagram illustrating one embodiment of a method 300 for speech reconstruction or enhancement, brain reconfiguration, brain research, and brain damage diagnosis in accordance with the present apparatus 100 or system 200. As depicted, after starting 302 the session the method makes a speech or action 304 to the subject 202. The action request 304 may be made by a session guide 304 or by the system 200 and may be communicated to the subject 202 via any known audio or video device including without limitation a speaker, an earphone, or a visual display or by the session guide 204 under the direction or assistance of the system 200. The request 304 sometimes comprises speech, song, or other sound. The request 304 may comprise movement, rhythmic movement, or other action. The method 300 receives subject 202 response data 306 and monitors subject 202 physiological data 308. The patient response may comprise speech, music, rhythm, or action. The action may comprise rhythmic tapping, hand motion, body motion, head motion, facial motion or other type of physical action. In certain embodiments the patient response comprises a physiological reaction including without limitation heart rate, respiration rate, galvanic skin response and neurological response. In various embodiments method 300 digitally samples and stores the data 310, and deconstructs the data into subcomponents 312. The method 300 may isolate incorrect components 316, find the distance to improvements 318, weigh the difficulty of improvements 320, and correlate this information with physiological data 322. In certain embodiments the method 300 applies other decision making factors 323 in order to select the optimal improvements 324, and apply these to the affected subcomponents 326. The method may reconstruct the subcomponents 328 and query "have all responses?" 330. If yes, then the method 300 may move to session completion 330 and end 332. If no, the method 300 returns to request subject speech, or other action 302.

Physiological data may comprise any measurable indication of subject physiological or emotional state, including without limitation input from EEG, EGG, EKG, pulse rate monitor, respiration rate monitor, galvanic skin response monitor, MRI, and fMRI.

Other decision factors 323 may include interactions with new data and new decision making criteria. The decision making criteria may be stored in any repository including rules 116, session memory 114, internal memory 110 or data archive 108. Storage may be made in any form including electronic, crystal, DNA, biochemical, physical, or new forms currently unknown.

In various embodiments the system 200 is self-learning and updates the decision factors 323 with experience. System 200 experience may be unique to the current subject 202 and may include previous experiences with other subjects 202.

In some embodiments the subject 202's brain damage comprises aphasia. Physiological data may comprise neurological data Recovery from aphasia can be achieved through recruitment of either peri-lesional brain regions in the affected hemisphere or homologous language regions in the non-lesional hemisphere. For subjects 202 with large left-hemisphere lesions, recovery through the right hemisphere may represent the most promising path. The right hemisphere regions best equipped to contribute to this recovery process are the superior temporal lobe (important for auditory feedback control), premotor regions/posterior inferior frontal gyrus (important for planning and sequencing of motor actions and for auditory-motor mapping) and the primary motor cortex (important for execution of vocal motor actions). A major fiber tract called the arcuate fasciculus (AF) connects these regions reciprocally, but the AF tract is usually not as well developed in the non-dominant right hemisphere.

In various embodiments of the method 300 the monitoring of subject physiological data 308 measures stimulation or growth of the AF. The correlation with physiological data 322 may use these measurements and select optimal improvements 324, apply to affected subcomponents 326, and reconstructed subcomponents 328 accordingly, thus generating the new request 304 that is most effective in stimulating or strengthening the AF.

Figure 3B:
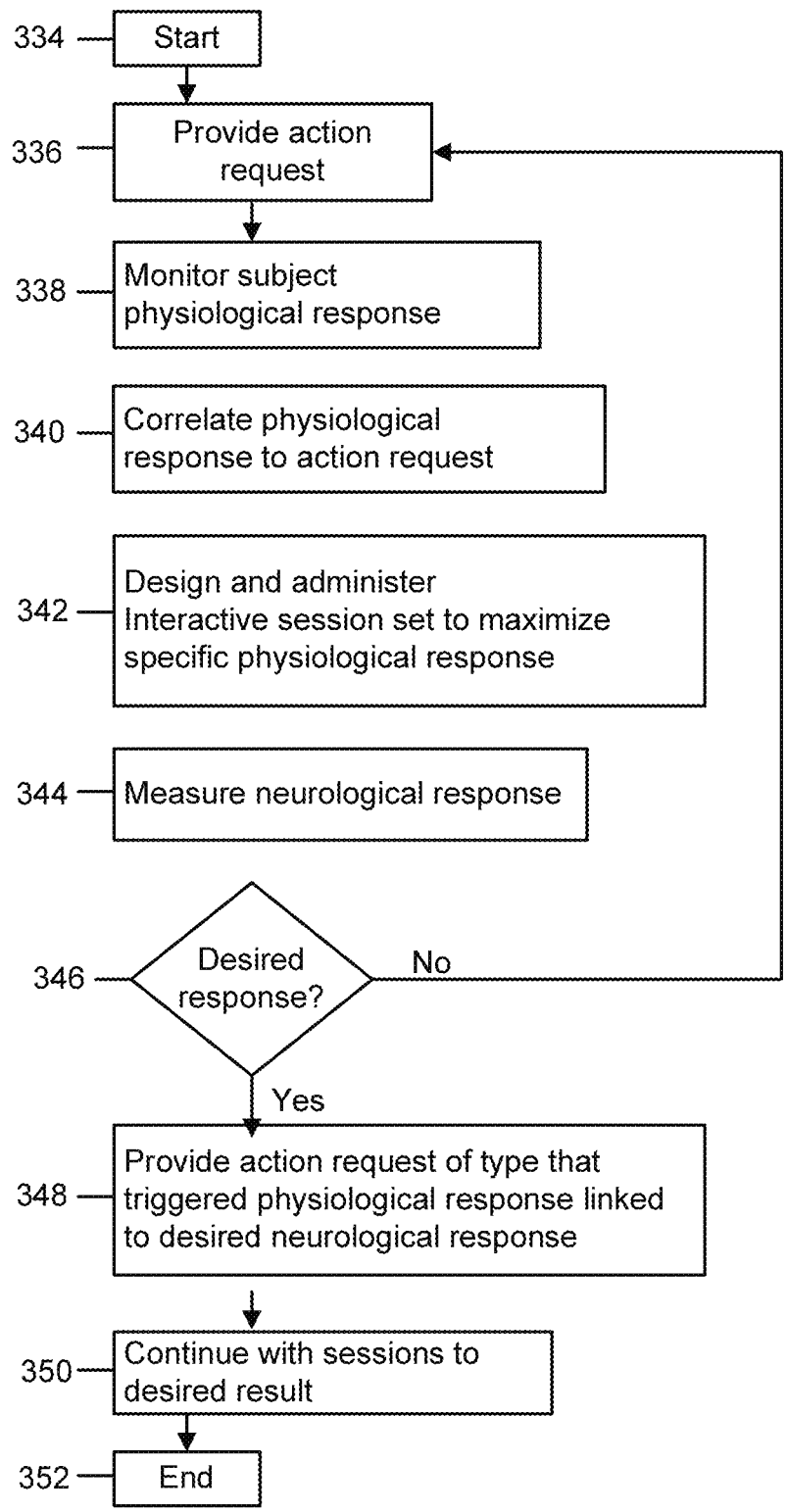
FIG. 3b is a schematic flow chart diagram depicting a further embodiment of a method for optimizing a neurological response in accordance with the present invention.

FIG. 3b is a schematic flow chart diagram depicting a further embodiment of a method 300 for optimizing a neurological response in accordance with the present invention. As depicted, the session may start 334 and provide an action request 336 to the subject. The subject's physiological response to the action request may be monitored 338. It is understood that the monitoring of the subject's physiological response to the action request includes monitoring of the subject's physiological response as the subject performs the suggested action. In some embodiments the physiological response may be brain waves. In certain embodiments various other physiological responses may be monitored. The physiological response may then be correlated with the action request 340. In various embodiments a set of interactive sessions that maximize a specific physiological response may be designed and administered 342 to the subject. The specific physiological response sometimes comprises a selected brain wave form.

The subject's neurological response may then be measured 344. In some embodiments the neurological response is cumulative. The cumulative neurological response may comprise brain changes or reconfiguration. The neurological response may be evaluated 346. If the desired neurological response is not observed the method 300 may return to provide a new action request 336. In some embodiments the new action request 336 is a different type of action than the action that failed to further the desired neurological response. If the desired response is observed 346 the method 300 may provide further action requests 348 of the type that triggered the physiological response 338 linked to the desired neurological response. The method 300 may continue to provide such requests to the desired result 350 and ultimately end the treatment or session 352.

In some embodiments the monitoring 338 and correlation 340 is conducted in real-time using any method available in the art for measuring physiological response. In certain embodiments the neurological response, including without limitation AF stimulation and growth is measured 344 and evaluated 346 in real-time. In various embodiments the measurement 344 and evaluation 346 of the neurological response is delayed and may be cumulative, or may be a combination of real-time and delayed. For example, recorded EEG data showing brainwaves may be captured in real-time and recorded. This data may be correlated with the type of action request 336 that most strongly stimulates each type and configuration of brain wave. A series of subsequent sessions may then be designed and implemented 342 over a range of time with requests for action that maximize various identified brain waves. In some embodiments the range of time may be 1 session to 100 sessions including 1 to 5 session, 6 to 10 sessions, 11 to 15 sessions, 16 to 20 sessions, 21 to 25 sessions, 26 to 50 sessions, 51 to 75 sessions and 76 to 100 sessions or more. In certain embodiments the range of time may be from less than one day to one day, including from 1 minute or less to one hour, from one hour to two hours, from two hours to five hours, from five hours to ten hours, from ten hours to 15 hours from 15 hours to 20 hours and from 20 hours to 24 hours. In various embodiments the range of time may be from 1 day to one week, from one week to one month, from one month to three months, from three months to six months and from six months to a year or more.

Cumulative measurements of neurological response 344, sometimes comprising AF stimulation and/or growth, may be conducted at the end of the range or time for each set of wave-type maximizing sessions. If a desired neurological response is observed 346 the method 300 may then provide 348 the actions most effective in triggering the physiological response observably linked to the desired neurological response, for example AF stimulation and/or growth. In certain embodiments other types of brain reconfiguration may be measured and correlated to action requests.

Figure 4:
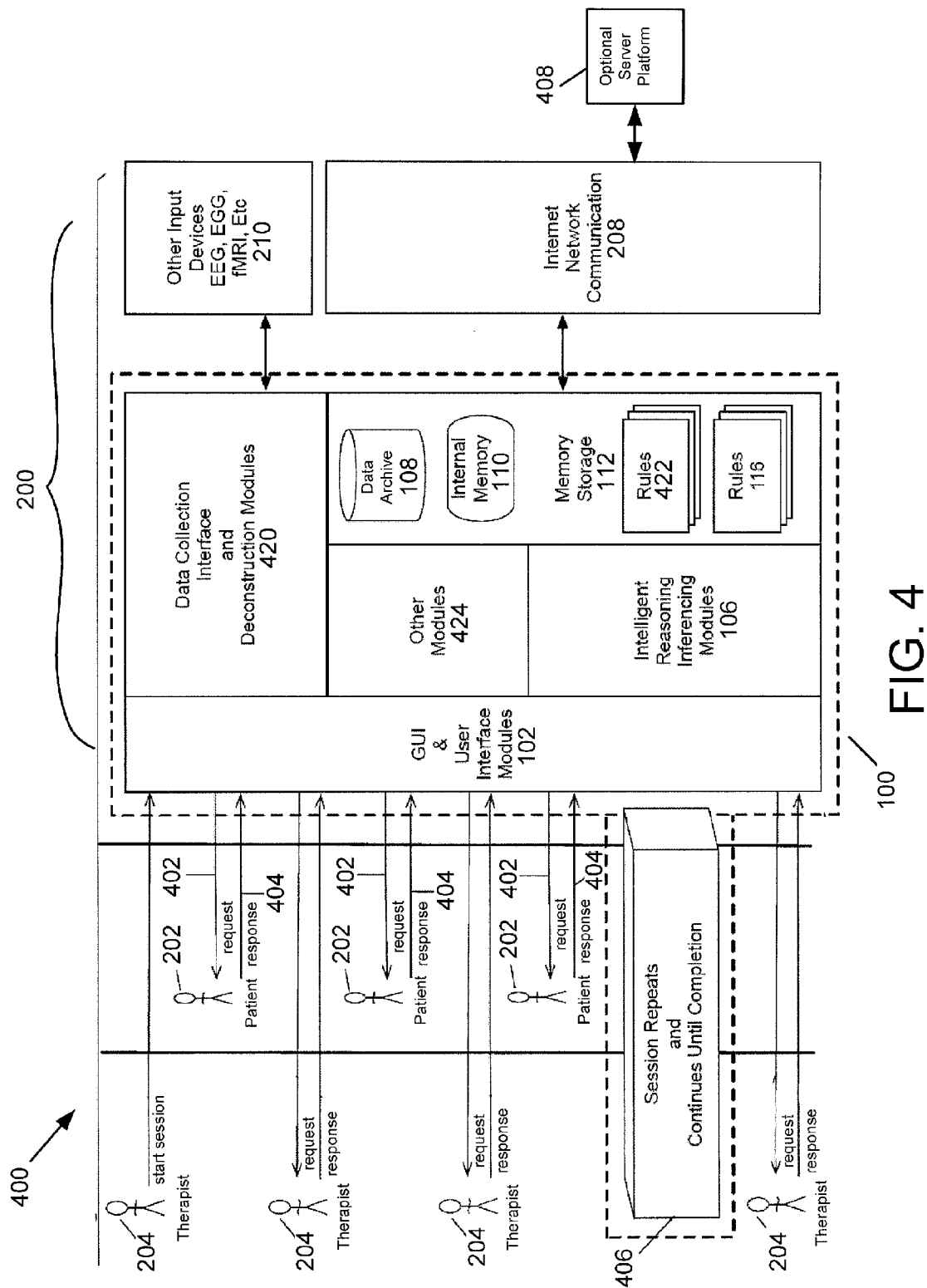
FIG. 4 is a schematic block diagram depicting one embodiment of an interactive therapy, research, or diagnostic session in accordance with the present invention.

FIG. 4 is a schematic block diagram depicting one embodiment of an interactive therapy, research, or diagnostic session 400 in accordance with the present invention. As depicted, the interaction therapy session 400 comprises a subject, 202, a session guide 204, an apparatus 100 a system 200, a request 402, a response 404, a session repeat and continuation until completion 406 and an optional server platform 408, in accordance with the present invention. In the depicted embodiment the apparatus 100 comprises a GUI and user interface module 102, a data collection interface and deconstruction module 420, an analysis module 106, a memory storage module 112 comprising a data archive 108, an internal memory 110, a rules module 116, and a rules module 422 as well as other modules 424. The system 200 further optionally comprises, as depicted, an internet/network communication channel 208 and other input devices 210.

In some embodiments the interactive therapy session 400 comprises Dynamic Adaptive Speech Reconstruction (DASR). The optional server platform 426 is sometimes remote, and may be a DASR website server platform. After a session type has been selected by the Session Guide 404 the Session Guide 404 may start the session 400, for example from an icon on a screen. The system 200 may then load the appropriate rule base for the selected session into the rules module 116 and the analysis module 106 may begin processing the rules. These rules, which are further defined below, provide the intelligence and knowledge that is necessary to drive the system and carry out the desired session. Initial rules encountered are responsible for starting up all the necessary components of the session 400. As depicted in FIG. 4 the system 200 has been turned on and subject data and information has been loaded into the system 200. In this non-limiting example, the session guide starts the interactive session 400, which is then controlled and directed by the system 200. The system 200 produces all audible or other requests to the subject 202.

In some embodiments once initialization has been completed the next set of rules 422 start the session 400 by making a request 402 of the subject 202. This request may be played from pre-recorded or synthetically generated audio or in the form of a visual or physical request stored in the system 200 or downloaded remotely, including from a DASR website server platform 408. The recorded request/example may be sent to the headphones or screen of both the session guide 204 and subject 202. If tapping of the hand is appropriate during the session, the system 200 may also activate a tapping instruction which may comprise a visual, auditory, vibrational, or tactile signal to any device known in the art. The system 200 then enters a wait and listen state waiting for the subject response or a timeout to occur.

In certain embodiments once a response 404 is received each data type is passed to its respective data processing modules which store the data in internal or long term memory 110. The data modules for each data type take their respective data and the modules deconstruct the data into the smallest meaningful unit. For words, the deconstructed unit may be a phoneme. For music the deconstructed unit may be a single pitch or note. For melody the deconstructed unit may be a single musical phrase. For rhythm the deconstructed unit may be a single beat.

By way of example, the system 200 issues a request 402 for the subject 202 to sing "Happy birthday to you". The system 200 begins by using a male voice. The request may play through both headsets to both the subject 202 and the Session Guide 204. The request 402 may include a tapping command to both the Session Guide and subject. The tapping command may be communicated in various forms, including without limitation auditory, visual, tactile, and vibrational. As depicted, the subject responds 404 by singing and tapping and the Session Guide hears the same response 404. The system 200 employs the various modules and databases to deconstruct and evaluate the response 404, to determine if the response 404 is correct, and if not what subcomponents are incorrect, and to reconstruct and issue a new request 402. In the depicted embodiment the data is collected, sampled, deconstructed, evaluated, and reconstructed in real time. Based on the above data information and other information gathered, the system 200's analysis module 106 uses all data to analyze the subject 202 progress and current state and uses its knowledge from its modules and databases to make decisions about the next step to take in the session. The session repeats and continues until completion 406.

The system 200 also evaluates the current data against prior subject/session histories and knowledge and uses this past information and knowledge to issue the next request 402 based on past success/failure rates and other data. For example the system 200 may also sense through conversing with the subject 202 that whenever the chosen voice was used in an action request 402 the subject 202's heart rate increased and his galvanic skin response was elevated indicating possible stress and a dislike for the type of voice being used by the invention. The system 200 may alter the voice type accordingly for future requests 402.

The interactive session 400 may also be used as a research and development tool by researchers 204 who may query the system 200 and extract cumulative data about all prior and current system sessions through access to the GUI and user interface module 102. Researchers 204 may thus have access to the various modules used to assist in evaluating data in the evaluation of new and innovative processes and methodologies for the treatment and study of aphasia.

Additionally, a researcher 204, can also employ a subject 202 in the research process and also use the real-time data capture and analysis capabilities in the research work, allowing for the capture of subject 202 data for use in research studies. In this case the intelligent processing capabilities of the apparatus 100 and the system 200 can be utilized to help analyze data and assist in solving research challenges and problems.

Figure 5:
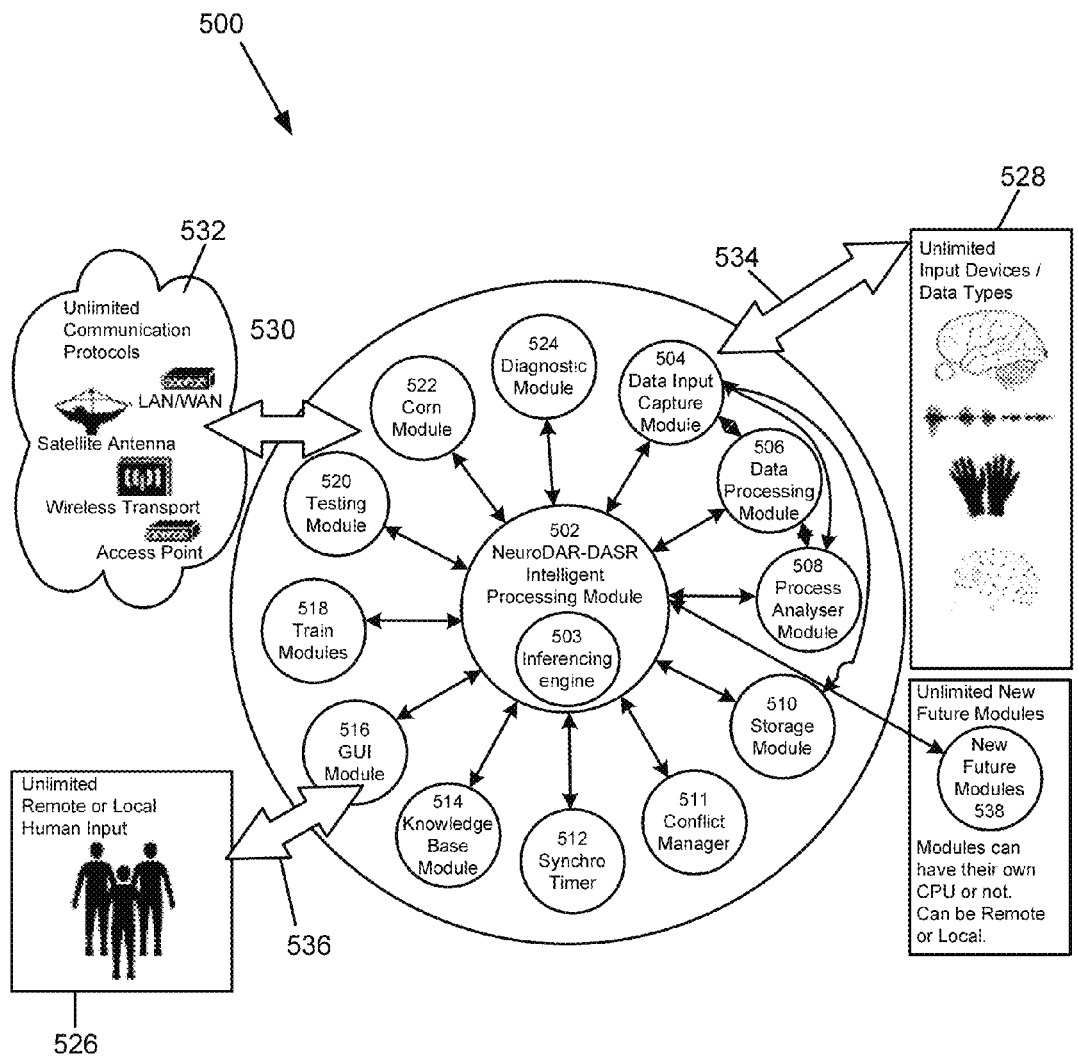
FIG. 5 is a schematic diagram depicting a high-level view of one embodiment of a system for speech reconstruction or enhancement, brain reconfiguration, brain research, and brain damage diagnosis enhancement in accordance with the present invention where said figure depicts the modularity and expandability of system modules.

FIG. 5 is a schematic diagram depicting a high-level view of one embodiment of a system 500 for speech reconstruction or enhancement, brain reconfiguration, brain research, and brain damage diagnosis enhancement in accordance with the present invention where said figure depicts the modularity and expandability of system modules. As depicted, here, the system 500 comprises an intelligent processing module 502, an inferencing engine 503, a data input capture module 504, a data processing module 506, a process analyzer module 508, a storage module 510, a conflict manager 511, a synchro timer 512, a knowledge base 514, a GUI module 516, a train module 518, a testing module 520, a communication module 522, a diagnostic module 524, remote or local human input 526, an input device 528, a remote communication channel 530, communication protocols 532, a device input communication channel 534, a human input communication channel 536 and may comprise new/future modules 538.

FIG. 5 depicts the high level design of one embodiment of the system 200, 500 is. The depicted modules may all communicate and work together to provide a functional system that is capable of Dynamic Adaptive Speech Reconstruction (DASR) and a variety of other functions such as post session research and development. As FIG. 5 depicts, the system 500 is designed in a modular fashion in order to facilitate expansion, scalability, and customization and the ability to adapt to unknown future requirements.

In certain embodiments the intelligent part of the system, the Intelligent Processing Module 502 is at the center of the system 500 and drives the directional control of the system, based on current and prior time synced data and utilizes rules in a set of knowledge bases 524 and an inference engine 503 in which the rules stored in the knowledge base 524 provide a way to infuse the knowledge necessary make decisions based on the existence of specific conditions found in the system 500. This intelligent process drives all facets of the system 500 from startup and system diagnostics, to patient prompting and subsequent patient data capture as well as data deconstruction and intelligent reasoning capabilities, for example when deciding the next direction to take in a patient session. Rules in a knowledge base 524 define the knowledge of the system and are responsible for driving the system. Rules in the knowledge base 524 can be preprogrammed in the initial apparatus 100 or system 200, 500, and can also be added to the system by a system administrator or researcher as new knowledge becomes known.

Rules allow the apparatus 100 or system 200, 500 to be trained and infused with reasoning knowledge without the need to have the entire invention redesigned each time new knowledge is added. Essentially, the rule base design allows expert knowledge to be placed into apparatus 100 or system 200, 500 for use in making intelligent processing decisions as the apparatus 100 or system 200, 500 performs its functions and duties. Furthermore, rule base 524 knowledge allows for the encapsulation and use of expert knowledge, that may exceed the capabilities and capacity of the human mind, to be used to complete complex and intricate real-time decision making functions and tasks.

In addition to being trainable by operators, the apparatus 100 or system 200 is capable of building its own rules or knowledge, based on current knowledge, data and newly identified trends. This is accomplished by adding specially designed rule bases to the knowledge base module 524 that are capable of analyzing existing data, rulebases and conditions and based on this information, these new rules are designed to actually create new sets of rules that can be used in the system to further its functionality and cause, thus allowing the invention to actually become self-aware and self-learning based on the experiences that it encounters.

Additionally, in some embodiments the apparatus 100 or system 200, 500 can accommodate for new types of data that may now or in the future become available or be determined to be beneficial. This is accomplished by adding new modules 538 that are programmed and designed to build new rules bases 52 on specific knowledge, acquire new data or handle other types of functions. Multiple knowledge bases 524 of rules can exist, each trained to handle different types of sessions such as training, testing, and research variants. The rules provide the reasoning knowledge to the inference engine 503 or intelligent processing module 502 that is necessary to reach conclusions and recommendations about what the patient should do.

In certain embodiments components are built around the concept of modules. A module is designed to perform a specific function. In various embodiments modules in the system are not finite and can be added and removed as the design dictates. Each module is capable of carrying out its specific functions autonomously but it also communicates with and takes direction from the main intelligent processing module 502. Additionally, each module can be processed by a system's central processing unit CPU/CPUs, or it can be processed by its own internal CPU or multiple CPUs.

The module concept allows for the addition and removal of modules without the entire redesign of the system as a whole. This is especially useful as the invention is designed to also be a research and development tool. During research, if it is determined that a new type of data input needs to be added to the system, a module can be designed and inserted into the invention which will handle the acquisition of a new data type. Additional modules can be added to deconstruct and reconstruct the new data if the new data has a totally new format than the data heretofore found and serviced with the invention.

Additionally, all data modules that are connected to the system maintain exact time synchronization from a time synchronization module 512, thus allowing all the data in the system to be assigned their respective data components in the right time synchronization so that all data, system-wide is correctly time aligned.

In some embodiments the intelligent processing module 502 comprises a NeuroDar-DASR intelligent processing module. The intelligent processing module 502 may receive data and input from the other modules and make action request decisions accordingly. In certain embodiments the inferencing engine 503 matches rules to data, conducts conflict resolution and selects the rules that will be activated or "fired" in subject therapy decisions. In various embodiments the data input capture module 504 captures incoming data including but not limited to speech, music, rhythm, action, sound, and physiological data. The data processing module 506 may process data, which processing may comprise deconstructing each type of data into its smallest meaningful components and directing the deconstructed data to the appropriate storage.

The storage module 510 may store raw and deconstructed data for access and use by the various other modules. In certain embodiments the synchro timer 512 captures the entry time of a data sample. In various embodiments the knowledge base module 514 comprises a rules database that the intelligent processing module 502 and the inferencing engine 503 may access in order to evaluate data and design action requests. The knowledge base module 514 sometimes comprises without limitation session memory from the current subject, data from other subjects, a therapy technique database, and an action database. In some embodiments the knowledge base 514 is continually updated by iterations of incoming data and "learns" with use. Multiple knowledge bases 514 of rules 116, 422 may exist, each trained to handle different types of sessions such as training, testing, and research variants. The rules 116, 422 may provide the reasoning knowledge to the intelligent processing module 502 in order to reach conclusions and recommendations for the subject.

In certain embodiments the conflict manager 528 comprises specialized conflict management rules configured to select which of the other rules 116, 422 to activate or "fire" when one or more of the other rules 116, 422 are in conflict. In some embodiments the other rules 116, 422 have been selected on the basis of data incoming from or relevant to the current subject 202 interactive session.

The GUI module 516 may accept human input. Human input 526 may comprise speech, music, rhythm, action, sound, physiological and other input. The human input communication channel 536 may carry the human input 526 to the GUI module 516 and may comprise any communication method or protocol known in the art. The data input device 528 may comprise any device configured to measure real-time or delayed input and may comprise without limitation a microphone, recording device, pressure sensor, rhythm sensor, keyboard, touch screen, video capture device, EEG, EGG, EKG, MRI, fMRI, and DTI. The device input communication channel 534 may be configured to carry input from such a device 538 to the data capture module 504. The communication protocol 532 may comprise any communication protocol known in the art including without limitation LAN/WAN, satellite communication, wireless transport, access point broadcast, fiber optic, wire, radio wave and microwave. In some embodiments the communication protocol 532 comprises new technology not presently known. The communication channel 530 may carry data between the communication protocol 532 and the communication module 522.

In certain embodiments the diagnostic module 524 accesses data from other modules including without limitation the storage module 510, the knowledge base module 514, and the testing module 520. The diagnostic module 524 may evaluate individual or combined data in order to diagnose the condition, progress, or prognosis of the subject 202.

The knowledge base 524, inference engine 107, or other elements of the system 200, 500 sometimes comprise various forms of intelligent reasoning architecture, including but not limited to cybernetics and brain simulation, cognitive simulation, logic based, anti-logic or scruffy, knowledge based, sub symbolic, statistical, intelligent agents, agent architectures and cognitive architectures, through search and optimization, logic, probabilistic methods for uncertain reasoning, classifiers and statistical learning methods, neural networks, control theory or expert systems in the solving of various problems including but not limited to deduction, reasoning, problem solving, knowledge representation, natural language processing, motion and manipulation, perception, social intelligence, general intelligence, and creativity.

The system 500 is designed in a modular fashion in order to facilitate expansion, scalability, and customization and the ability to adapt to unknown future requirements. Thus, the system 500 can accommodate new types of data that may become available or be determined to be beneficial to the operation of the system 500 either now or in the future. This may be accomplished by adding new modules 538 that may be designed and programmed to build new rules bases on specific knowledge, acquire new data or handle other types of functions. The expansion capability may be useful as in some embodiments the system 500 is a research and development tool. During research, if it is determined that a new type of data input needs to be added to the system 500, a new module 532 can be designed and inserted into the system 500 to accommodate the new data type. In some embodiments additional new modules 538 can be added to deconstruct and reconstruct the new data, for example if the format of the new differs from the format of data previously input into the system 500.

In some embodiments each module is capable of carrying out its specific function autonomously but also may communicate with and take direction from the main intelligent processing module 502. In certain embodiments, each module is processed by a system's central processing unit CPU/CPUs. In some embodiments each module relies on its own internal CPU. The various modules sometimes rely on multiple CPU's or on other systems. The modules may employ the Internet Cloud or other remote location, or facility, or use a server platform such as optional server platform 426. In some embodiments the optional server platform comprises a DASR website.

Figure 6:
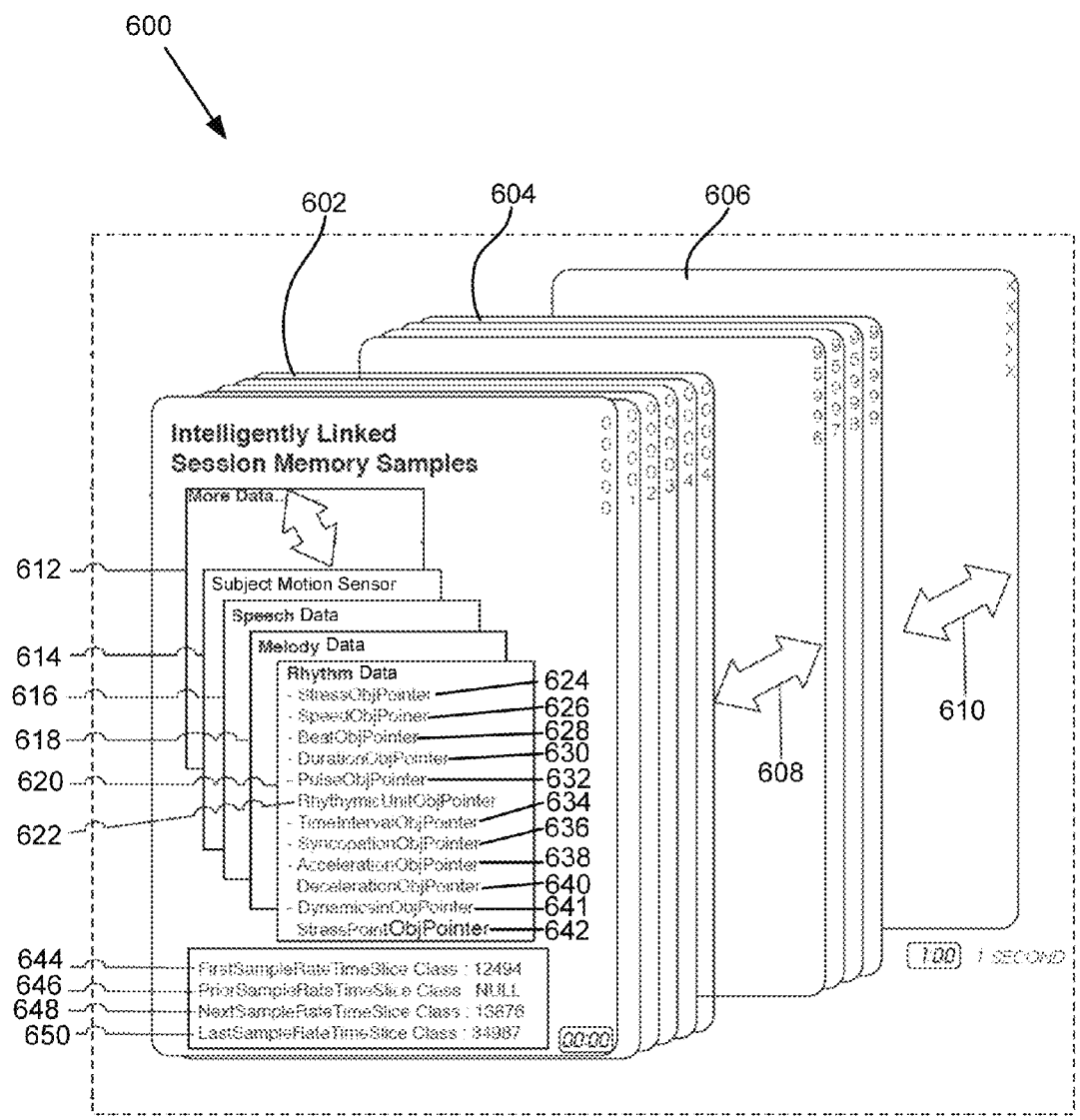
FIG. 6 is a schematic block diagram depicting one embodiment of a data storage architecture used to capture (sample) incoming data as well as objects for storage in accordance with the present invention.

FIG. 6 is a schematic block diagram depicting one embodiment of a data storage architecture used to capture (sample) incoming data as well as objects for storage in accordance with the present invention. As depicted, the data storage architecture 600 comprises time slice data sample software objects 602, 604, 606, and place holders 608 and 610 representing a software object for each time slice data sample from, in certain embodiments, one to 96,000 per second or higher. In some embodiments single time slice software object 602 comprises motion sensor data 614, speech data 616, melody data 618, rhythm data 620, a rhythmic unit object pointer 622, a stress object pointer 624, a speed object pointer 626, a beat object pointer 628 a duration object pointer 630, a pulse object pointer 632, a time interval object pointer 634, a syncopation object pointer 636, an acceleration object pointer 638, a deceleration object pointer 640, a dynamics object pointer 641, a stress point object pointer 642, a first sample rate time slice class 644, a prior sample rate time slice class 646, a next sample rate time slice class 648, and a last sample rate time slice class 650.

In other embodiments a single time slice software object 602 may also contain any number of other object pointers and is not limited to the above mentioned pointers, 612, 614, 616, 618, 620, 622, 644, 646, 648 and 650. In some embodiments architecture 600 may comprise time slice data sample software objects 602, 604, 606, and place holders 608 and 610 that are sampled at a rate different than 96,000 per second.

In certain embodiments the software objects 602, 604, and 606 are created dynamically in time sequence, one object for each time sample, in some embodiments 96,000 samples for each second of sampling. Each time slice sample software object, may comprise, for example, unique data classes 612, 614, 616, 618, 620, 622 as well as memory pointers 624, 626, 628, 630, 632, 634, 636, 638, 640, 641, 642 to each individual data if it is being captured. The memory pointers may point to the appropriate storage area containing the actual data for that component of the sample, serving, in essence, as an index to a data library. For example, the stress object pointer 624 for a given time slice would point to the stress data stored for that unique time slice and the speed object pointer 626 would point to the speed data stored for that unique time slice. Every time slice generates a time slice data software object and stores the associated data for that unique time slice.

All data modules may be time synchronized so that when they receive data, which can come in at different time offsets, the modules sense exactly at what time in the sampling timeline the data is received. In certain embodiments the synchronization alignment information is critical as the deconstructed data needs to be placed in the appropriate time sample software object 602, 604, 606, that represents the time the data was received. The initial placement of the data at the proper offset in the sample position may be essential to keeping all data synchronized throughout the entire session.

The time slice sample software objects e.g. 602, 604, 606 may be linked together by pointers 644, 646, 648, 650 based on sampling time. In some embodiments the first sample rate time slice class 644 comprises the first time slice sample software object data in a data set collected at the designated sampling rate. The prior sample rate time slice class 646 comprises time slice sample software object generated immediately previous to the current sample in the data set collected at the designated sampling rate. The next sample rate time slice class 648 comprises the time slice sample software object collected immediately after the current sample of data in the data set collected at the designated sampling rate. The last sample rate time slice class 650 comprises the final time slice sample software object in the data set collected at the designated sampling rate. In some embodiment the sample rate time slice classes 644-650 organize each time slice sample software object in time, relative to the other time slice samples and enable navigation of the time slice sample software objects on the basis of collection time.

As a module deconstructs raw data the deconstructed subcomponents may be stored in locations pointed to be the relevant pointer 624-642, so that the footprint of any software object remains small. If no data is recorded in a given time slice sample than the pointer to the associated sample rate time slice class 644-650 will be marked with a value of NULL. Such pointers enable processing to jump between "active" time slice sample software objects e.g. 602, 604, 606 continuing to the end of sampling, or 96,000 in some embodiments of one second of sampling. In some embodiments each time slice sample data software object comprises a pointer 644-648 to the first sample for the sampling period, as well as to the prior, subsequent, and last sample.

Figure 7:
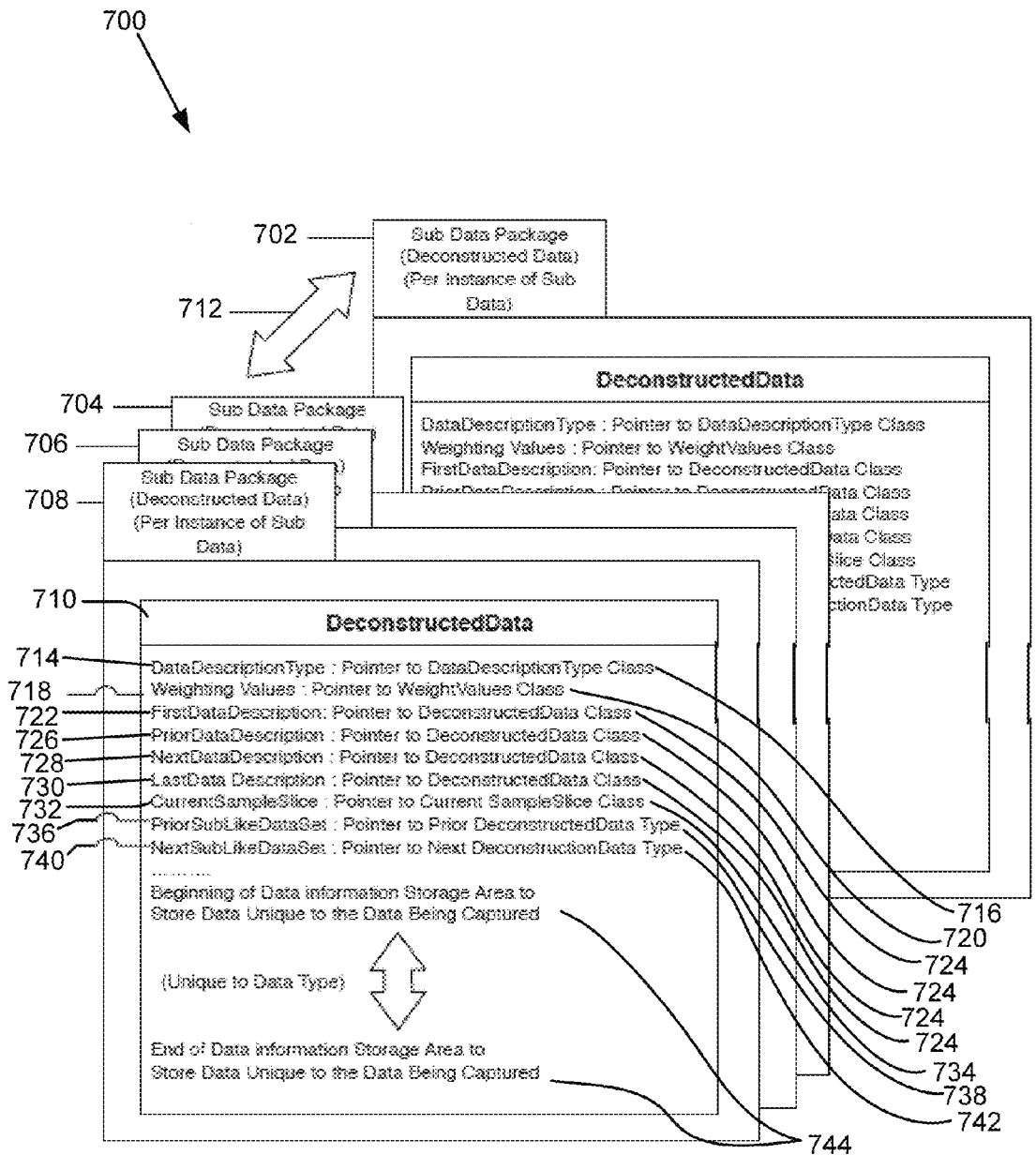
FIG. 7 is a schematic block diagram depicting one embodiment of an architecture showing objects pointed to by sampling object pointers found in FIG. 6. These objects hold data information about data types that are being sampled.

FIG. 7 is a schematic block diagram depicting one embodiment of an architecture 700 for deconstructed data. As depicted, the architecture 700 comprises a sub data package of deconstructed data 702, 704, 706, and 708, an example of deconstructed data 710, and a place holder 712 representing a sub data package of deconstructed data for each instance in which a sub data package is generated. As here depicted sub data package 708 comprises deconstructed data 710 comprises a data description type 714, a pointer to a data description type/class 716, a weighting value 718, a pointer to a weighting values class 720, a first data description 722, a pointer to a deconstruction data class 724, a prior data description class 726, a pointer to deconstruction data type/class 724, a next data description 728, a pointer to a deconstruction data/class 724, a last data description 730, a pointer to a deconstruction data class 724, a current sample slice 732, a pointer to a current sample slice class 734, a prior sub-like data set 736, a pointer to prior deconstruction data type 738, a next sub-like data set 740, a pointer to a next deconstruction data type 742 and a storage area for data unique to the class/type of data being captured 744.

The data unique to the class/type of data being captured 744 may be, for non-limiting example, pitch data for melody, interval data for rhythm, phoneme data for a word, or stimulation data for a neurological response. Sub data packages may be dynamically created and reconfigured according to the type of data being stored.

In some embodiments pointers 624-642 each link to the corresponding areas in 602, 604, 606, etc. Subdata packages 702, 704, 706, 708 etc. are linked by pointers 722-730. For example, a beat object pointer 628 may point to the first instance of a beat sub data package and a beat object pointer 628 from a later sample may point to a later instance of a beat sub data package.

The data description time classes 722-730 with their associated pointers 724 enable the sub data packages to be navigated, or "walked through" by, for example, beat. Thus, the beat subcomponents of a subject 202 response may be analyzed in time order, facilitating the identification of improvements, regressions, and trends.

In various embodiments these pointers 738 and 742 enable the system 200, 500 to identify when the immediately prior occurrence 736 and the next occurrence 740 of the same data type occurs in the time samples. This may facilitate identification of starting points of data of the same type without having to do intensive memory scanning and extrapolation. This efficiency with respect to access to session data may be critical may assist the inference engine 107, 503 and the knowledge base module 514 in recalling any amount of data quickly for analysis for real-time session direction decisions.

A prior sub-like data set 736 may be a prior data set comprising data of the same or a similar type to the data in the current sub data package and may be accessed by the pointer to the prior deconstructed data type 738. The next sub-like data set 740 may be a next data set comprising data of the same or a similar type to the data in the current sub data package and may be accessed by the pointer to the next deconstruction data type 744.

Figure 8:
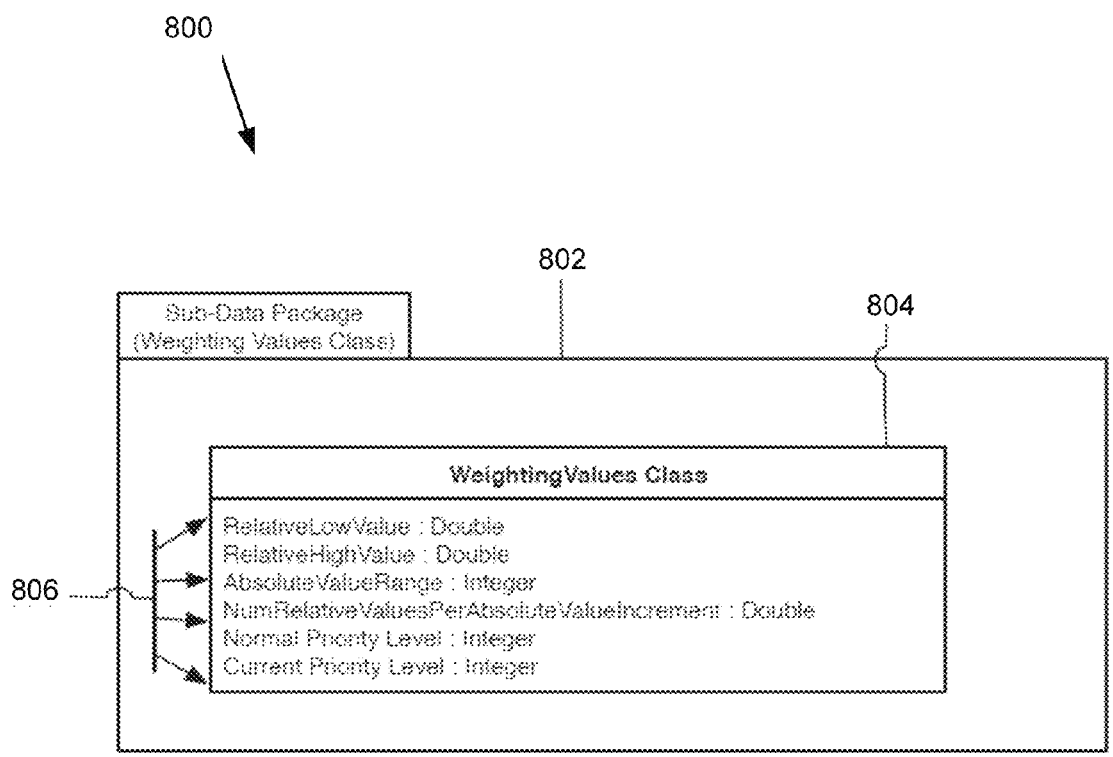
FIG. 8 is a schematic block diagram depicting one embodiment of an architecture for a weighting values class in accordance with the present invention.

FIG. 8 is a schematic block diagram depicting one embodiment of an architecture 800 for a weighting values class in accordance with the present invention. As depicted, the architecture 800 comprises a sub-data package for a weighting values class 802, and a weighting values class memory object 804 comprising weighting information 806 for a data class. The pointer to the weighting values class 720 invokes the weighting values class memory object 804 with its relevant weighting information 804.

Figure 9:
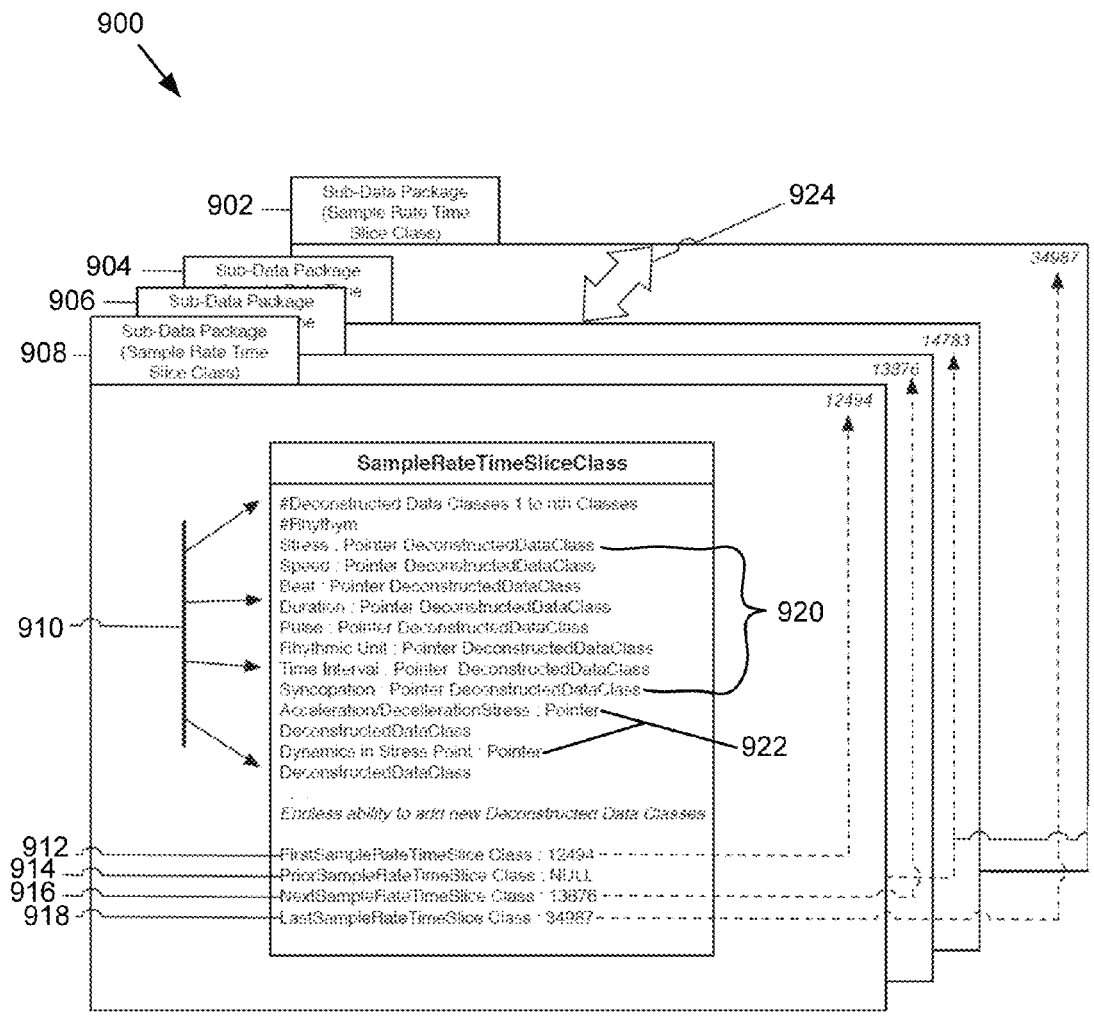
FIG. 9 is a schematic block diagram depicting one embodiment of a rhythm data class architecture in accordance with the present invention.

FIG. 9 is a schematic block diagram depicting one embodiment of a rhythm data class architecture 900 in accordance with the present invention. As depicted, the rhythm data class architecture 900 comprises a software object 902, 904, 906, 908 (620) storing deconstructed rhythm class data 910 and sample rate time slice class data pointers 912, 914, 916, 918. In some embodiments the rhythm class data comprises stress, speed, beat, duration, pulse, rhythmic unit, time interval, and syncopation, each accessed by a deconstructed data class pointer 920. The deconstructed rhythm class data may further comprise acceleration/deceleration stress and dynamics in stress point, each accessed by a pointer 922.

Because in various embodiments all data is sampled in time slices there will exist a unique deconstructed data software object 902, 904, 906, 908 for each time sample. In certain embodiments the deconstructed data software objects are also dynamically allocated as needed in order to capture the entire duration of the data 920. The deconstructed data software objects may be linked through pointers 912, 914, 916, 918 that enable the entire duration of the individual data to be referenced and accessed. As depicted, in software object 910 the pointers 912, 914, 916 and 918 reference offsets into the array of deconstructed data software objects. Pointer 912 points to the first occurrence of a data object 12494. Pointer 914 references the prior object which in this case us marked NULL as software object 908 is the first occurrence and there are no previous objects associated with this data stream. Pointer 916 references or points to the next object in the data stream, here sample number 13876. Pointer 918 points to the last software object in the data stream which is in this sample number 34987. As depicted the pointers 912, 914, 916, 918 allow for quick access to the data information by the system 200, 500 in order to evaluate the data and to make real-time decisions for the session.

In some embodiments, in order to reduce memory overhead and also CPU processing time, during those time periods of no data the system 200, 500 does not create time sample software objects 902, 904, 906, 908. Instead it places a NULL value in the data area for the appropriate data. In certain embodiments if there is data of a type that does not have a sample in each time slice (i.e 96,000 contiguous times per second) there will be "breaks" in the existence of pointers to the deconstructed data of that type. In this instance if the system 200, 500 were to try to trace the data samples using the information contained for that data class in the time slice sampling objects 902, 904, 906, 908 the system 200, 500 would encounter "breaks' in the chain of samples. For example, if a finger tapping were to occur 3 times in one second then there would be three bursts of rhythm data for finger tapping with lulls between. The finger tapping rhythm data input would thus not occur 96,000 times during that particular one second sampling period. In order to identify and easily handle breaks in which there is no data to collect, the system 200, 500 would place a NULL value in relevant sample rate time slice class, 914. The software pointers 912-918 link data samples temporally, enabling the system 200. 500 to "walk" through the data samples for a deconstructed data type, even if the samples skip or bypass some of the 96,000 samples per second. This may facilitate fast tracking and walking through memory information for deconstructed data that has periods input silence.

Figure 10:
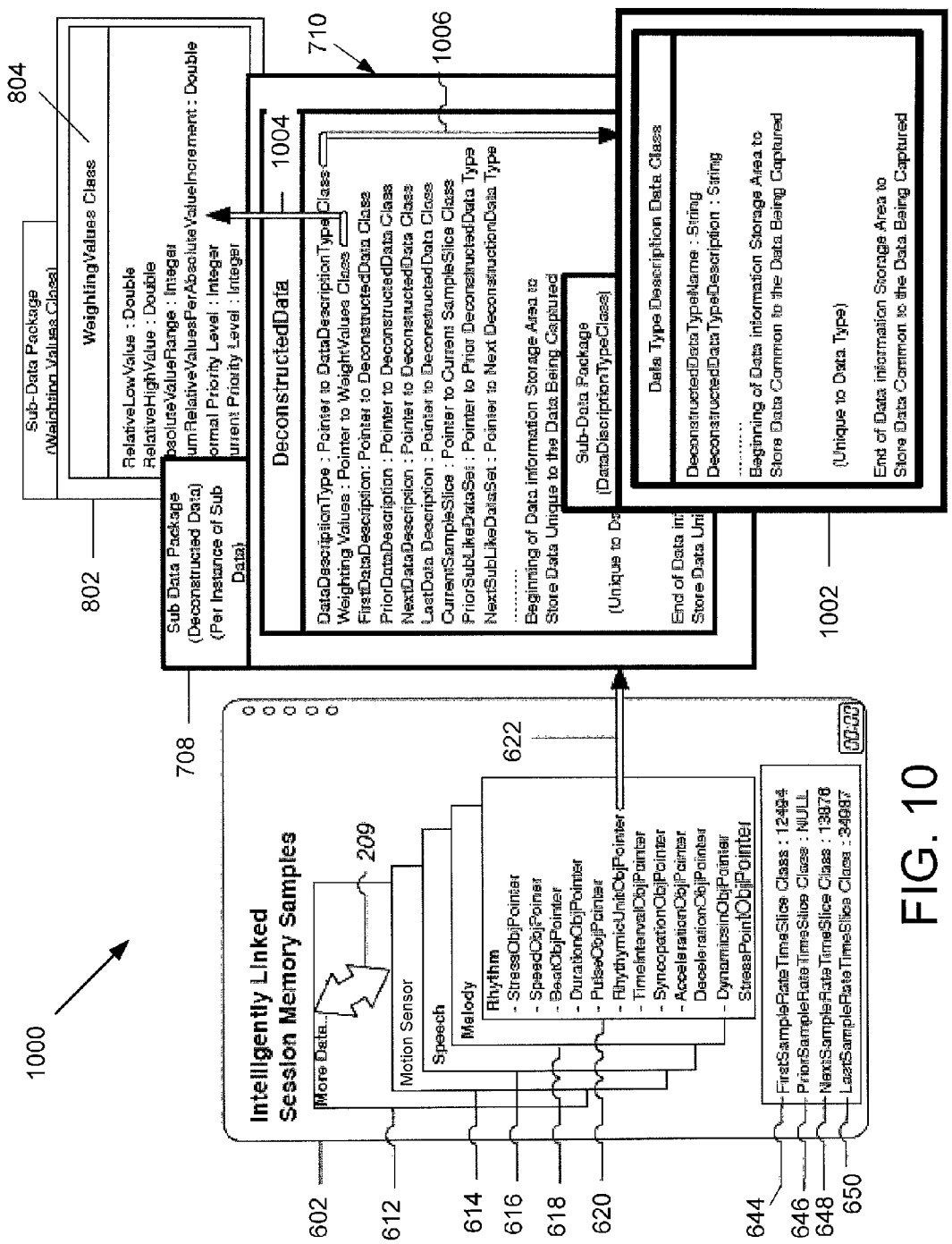
FIG. 10 is a schematic block diagram depicting one embodiment of the relationship between intelligently linked data time sample software objects in accordance with the present invention.

FIG. 10 is a schematic block diagram depicting one embodiment of the relationship 1000 between intelligently linked data time sample software objects in accordance with the present invention. As depicted, the relationship 1000 comprises a time sample software object 602, as depicted in FIG. 6, rhythm data 620, a sub data package of deconstructed rhythm data 708, a sub-data package for a weighting values class 802, a sub-data package for a data description type class 1002, a rhythm unit object pointer 622, a pointer 1004, and a pointer 1006.

In the depicted embodiment the time sample software object 602 is created for each time sample (default 96,000 per second). The data storage information may begin in the time sample software object 602 and extend outward through a series of pointers. For each data type, depicted here as rhythm data 620, there are pointers to the associated deconstructed data. For example, for rhythm data 620, there is a sub-pointer for a deconstructed component designated rhythmic unit 622. The sub-pointer 622 points to a sub data package for rhythm 708 configured to hold the information about rhythmic unit data. The rhythmic unit object 708 comprises the pointer 1004 to a sub data package for weighting values 804. The pointer 1006 points to a sub data package for a data description type class.

As shown, the rhythm data 620 has been deconstructed into stress, speed, beat, duration, and other components. Each of these and other types of data may be further deconstructed, forming additional "layers" of information with various sub data packages and pointers. Pointers (not shown) may point to the temporal (first, prior, next, and last) deconstructed data classes, as well as to data unique to the sample. In this manner data from each time slice sample may be captured, deconstructed, stored, accessed, and further deconstructed to any necessary level.

Figure 11:
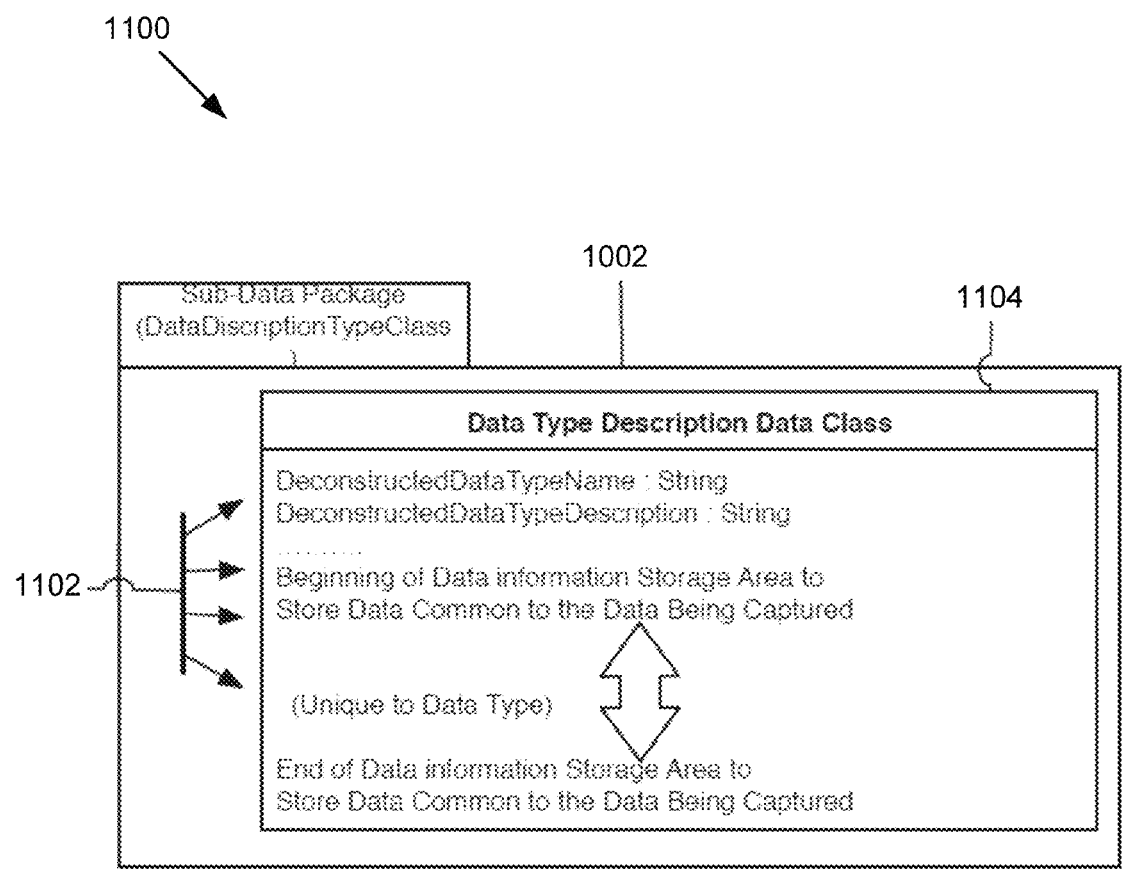
FIG. 11 is a schematic block diagram depicting one embodiment of a data type description software object that represents unique information about deconstructed data in accordance with the present invention.

FIG. 11 is a schematic block diagram depicting one embodiment of a data type description software object 1100 that represents unique information about deconstructed data in accordance with the present invention. As depicted, the software object 1100 comprises a sub-data package for a data description type class 1002, a data type description data class 1104, and data type description information 1102. In some embodiments the software object 1100 represents the unique information about each deconstructed data.

Figure 12:
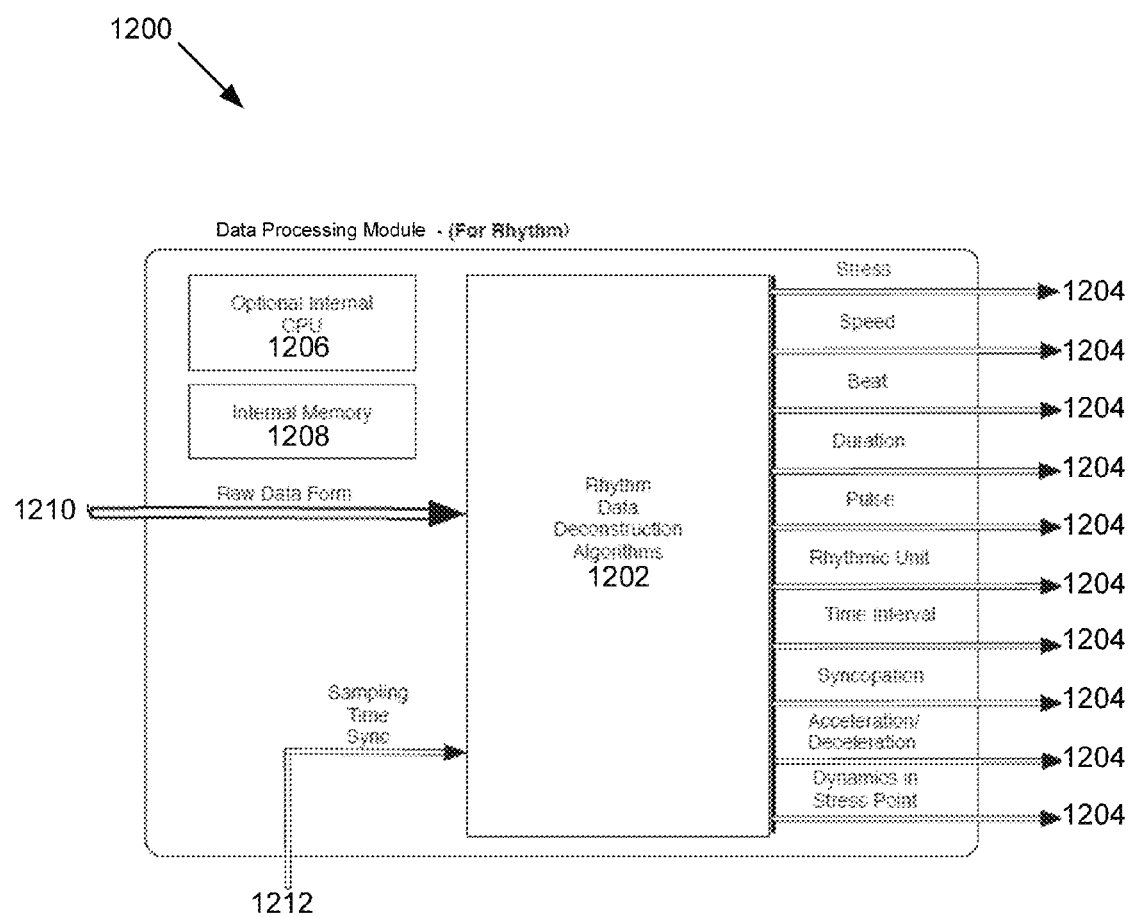
FIG. 12 is a schematic block diagram depicting one embodiment of a data deconstruction processing module for rhythm in accordance with the present invention.

FIG. 12 is a schematic block diagram depicting one embodiment of a data deconstruction module for rhythm 1200 in accordance with the present invention. As depicted, the data processing module for rhythm 1200 comprises rhythm data deconstruction algorithms 1202, deconstructed rhythm elements 1204, an optional CPU 1206, and internal memory 1208, and raw data 1210 and a sampling time sync 1212.

In the depicted embodiment the raw data 1210 enters the module 1200 and is sampled at a rate set by the sampling type sync 1212. The data samples for rhythm are passed to the rhythm data deconstruction algorithms 1202 and deconstructed into their component elements. There may be at least one data deconstruction module for each high level data type, including but not limited to speech, melody, rhythm, sensory input and physiological input. In some embodiments as data is received from the subject, it is passed to its respective data processing module 1200, which may be active and waiting for data 1210 to be input. As the data processing module 1200 receives data 1210, the data processing module 1200 in real-time stores or buffers the data in memory 1208 and then uses its internal functionality 1202 to deconstruct the data into its lowest level components 1204.

Each type of data processing module has individual internal deconstruction algorithms that are used to deconstruct the specific data type. In the depicted embodiment the rhythm data 1210 is deconstructed into deconstructed rhythm elements 1204 including without limitation stress, speed, beat, duration, pulse, rhythmic unit, time interval, syncopation, acceleration/deceleration, and dynamics in stress point. The deconstructed rhythm elements 1204 may then be stored in the internal memory 1208 or elsewhere and may be accessed by the analysis module 106, the inferencing engine 107, 503, the intelligent processing module 507 or other system 200, 500 modules or components for evaluation and use.

Figure 13:
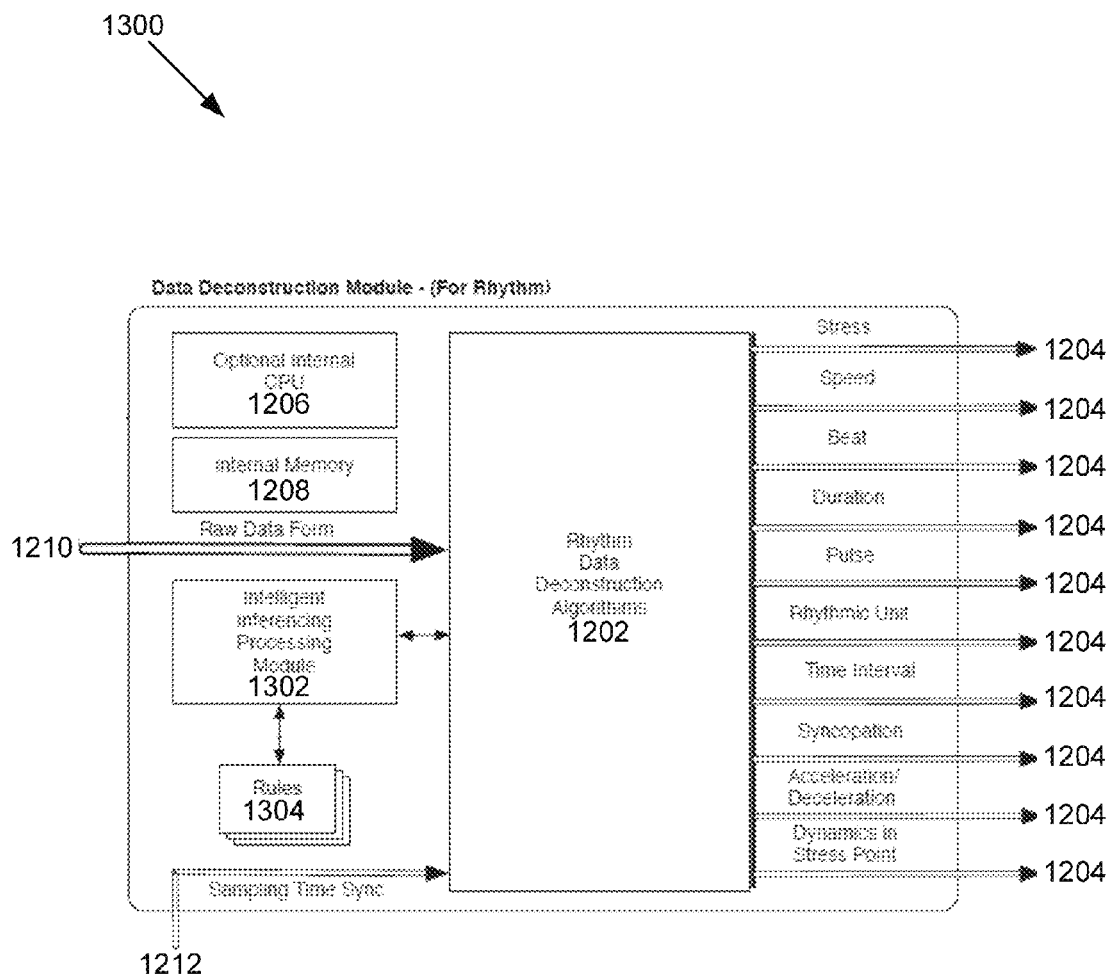
FIG. 13 is a schematic block diagram depicting one embodiment of an expanded data deconstruction module that has an optional inferencing engine and rule base in accordance with the present invention.

FIG. 13 is a schematic block diagram depicting one embodiment of an expanded data deconstruction module that has an optional inferencing engine and rule base in accordance with the present invention. As depicted, the expanded data deconstruction module 1300 comprises rhythm data deconstruction algorithms 1202, deconstructed rhythm elements 1204, an optional internal CPU 1206, an internal memory 1208, raw data 1210, a sampling time sync 1212, an intelligent inferencing processing module 1302, and a rules base 1304.

Modules are designed to be dynamic and customizable. Furthermore, modules may contain their own intelligence and in some embodiments replicate various functions of the system 200, 500 within the module itself in order to perform tasks and functions that require intelligent decision making processes. In certain embodiments, the module contains its own inferencing engine 1302 which communicates and interacts with its own internal rules where the inferencing engine 1302 helps drive and run the various module algorithms. In the depicted embodiment the intelligent inferencing processing module interacts with the data deconstruction algorithms 1202 and the rules base 1304 to further process the deconstructed data 1204.

Figure 14:
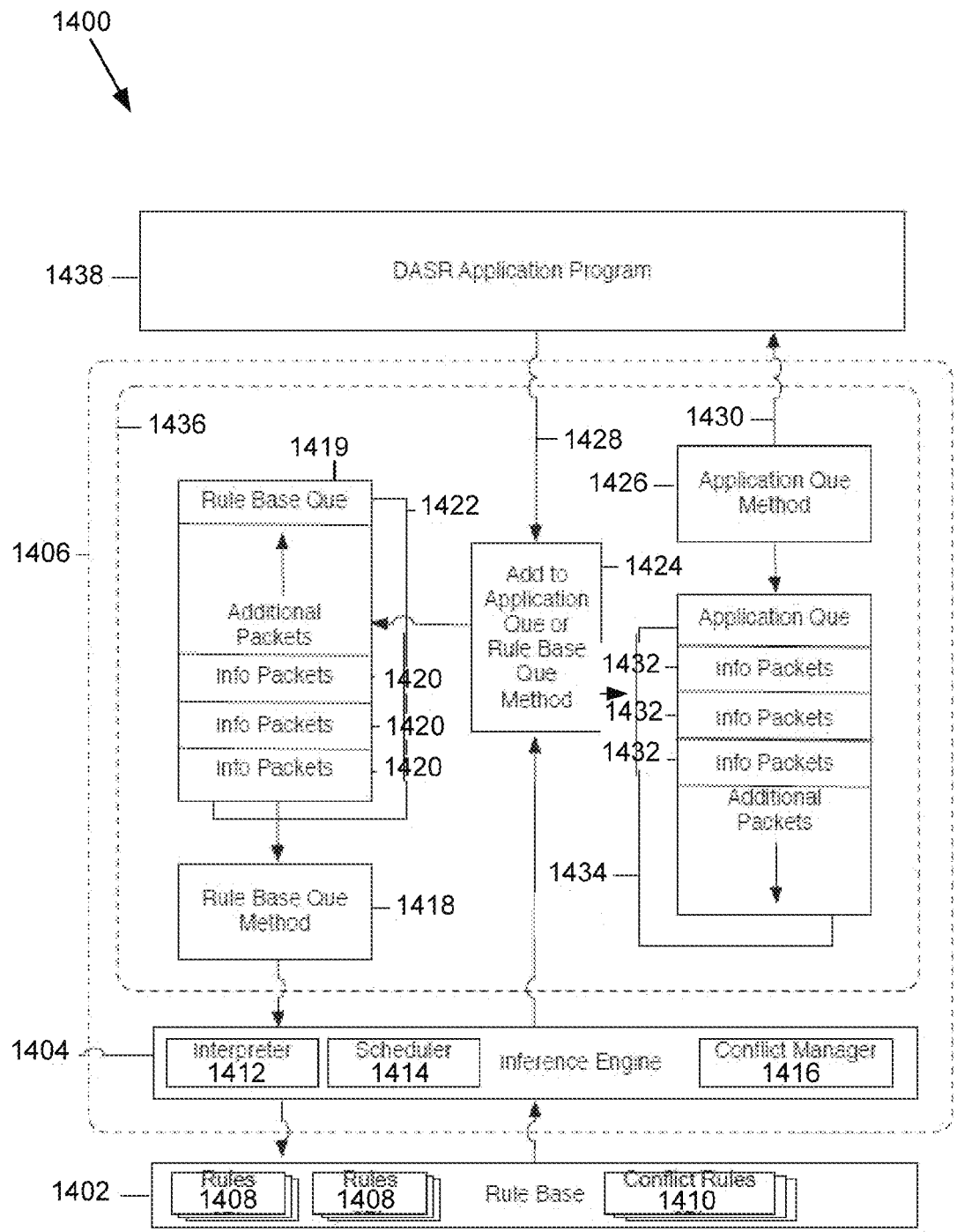
FIG. 14 is a schematic block diagram depicting one embodiment of an intelligent reasoning module in accordance with the present invention.

FIG. 14 is a schematic block diagram depicting one embodiment of an intelligent reasoning module 1400 according to the present invention. As depicted, the intelligent reasoning module 1400 comprises a rule base 1402, rules 1408, conflict rules 1410, an inference engine 1404, an interpreter 1412, a scheduler 1414, a conflict manager 1416, a processing module 1406, a rule base que 1422, information packets 1420, a rule base que method 1418, an application que method 1430, application que information packets 1432, an addition module 1424, a processing module 1436 and interfaces to an application program 1438.

In some embodiments the rule base 1402 comprises a set of knowledge rules 1408 which contain the system knowledge. The inferencing engine 1404 processes the rules through a processing module 1436 to make intelligent decisions. The processing module 1436 also receives input from the time synchronizing module in the application program 1438 and communicates to the application program 1438. The application program 1438 is sometimes a DASR application program. In certain embodiments the inference engine 1404 is the controlling mechanism responsible for processing all the rules 1408 in the system 200, 500. The compilation of rules 1408 may be called a rule base 1402. Actual decisions and action are taken through the rules 1408 and the knowledge contained within them. The inference engine 1404 directs the processing of the rules 1408 that comprise the rule base 1402 of the system 200, 500.

In certain embodiments the Inference engine 1402 comprises the interpreter 1412, the scheduler 1414, and the conflict manager 1416. The interpreter 1412 may execute chosen functions or actions based on the application of corresponding base rules 1412, 1416. The scheduler 1414 may maintain control over system 200, 500 plans and actions by calculating the effects of applying various inference rules 1412, 1416. Such rules 1412, 1416 may be subject to rule priorities or other criteria including without limitation the current state of the system, i.e. type of session, startup mode, research and query mode, post session data batch processing mode etc. In some embodiments the conflict manager 1416 functions to maintain a consistent representation of an emerging solution, including action requests to the subject 202.

The inference engine 1404 can be described as a finite state machine where a minimum of three states exist. The three initial states are 1). match rules, 2). select rules, 3). execute (or fire) rules. The first state attempts to match all rules 1408 in the rule base 1402 that satisfy the current contents of the data storage architecture 600. The second stage selects the rules 1408 that meet the criteria for execution because the required data conditions exist for the rules 1408, 1410 to execute. All the rules 1408 that are found to be candidates for execution (or firing) are then passed to the conflict manager 1416 for processing. The conflict manager 1416 makes decisions on which rules 1408 to fire/execute based on a variety of criteria that are stored in special conflict resolution rules 1410. In this state the inference engine applies selection criteria or strategies from the conflict rules 1410 to determine which functional rules 1408 are to be executed and which are not when conflicting rules 1408 are all candidates for execution. Since the contents of the data storage architecture 600 is usually updated as rules 1408 are fired, a new set of rules 1408 will match during the next and each subsequent cycle after current rule actions are performed.

The inference engine 1404 may be an expert system that is capable of both forward and backward chaining. In forward chaining system 200, 500 has no pre-determined outcome, and works to find a solution by investigating problems progressively in a fault diagnosis mode. In backward chaining the inference engine 1404 has a target outcome. In this case the inference engine 1404 starts from the goal and works backward toward the solution.

In some embodiments the processing module 1436 contains the internal memory 110 and que management facilities 1418, 1424, 1430 that the inference engine 1404 uses to manage and position rule 1408, 1410 components when a knowledge session is being processed. The inference engine 1404 scans and extracts appropriate rules 1408, 1410 and adds 1424 their components to an application queue 1434 or a rule base queue method 1418. The rule base que method 1418 may process, parse and manage rules 1408 and their components and place the appropriate information packets 1420, 1432 on special queues 1422, 1434. In some embodiments information packets 1420, 1432 are parts of a rule 1408 that require testing or information.

As depicted, que 1422 processes info packets 1420 that allow the rule 1408 to continue processing and working to a successful completion or fire/action. Que 1434 may be the que in which rule actions or directives have been issued and are waiting to be carried out and executed. These actions may be passed to the application program 1438 for execution via the application que method 1430.

Que 1422, in certain embodiments, manages internal rule information and passes the results of specific information packets 1420 back to the inference engine 1404 through the rule base que method 1418 so that the inference engine 1404 may continue to process and include or eliminate rules 1408 in the inferencing process. The add to application que/rule base que method 1424 may communicate with the inference engine 1404 and the application program 1438. In some embodiments either or both of queues 1422 and 1432 are capable of growing dynamically in order to accommodate the complexity that the inference engine 1404 and rule base 1402 may require.

Figure 15A:
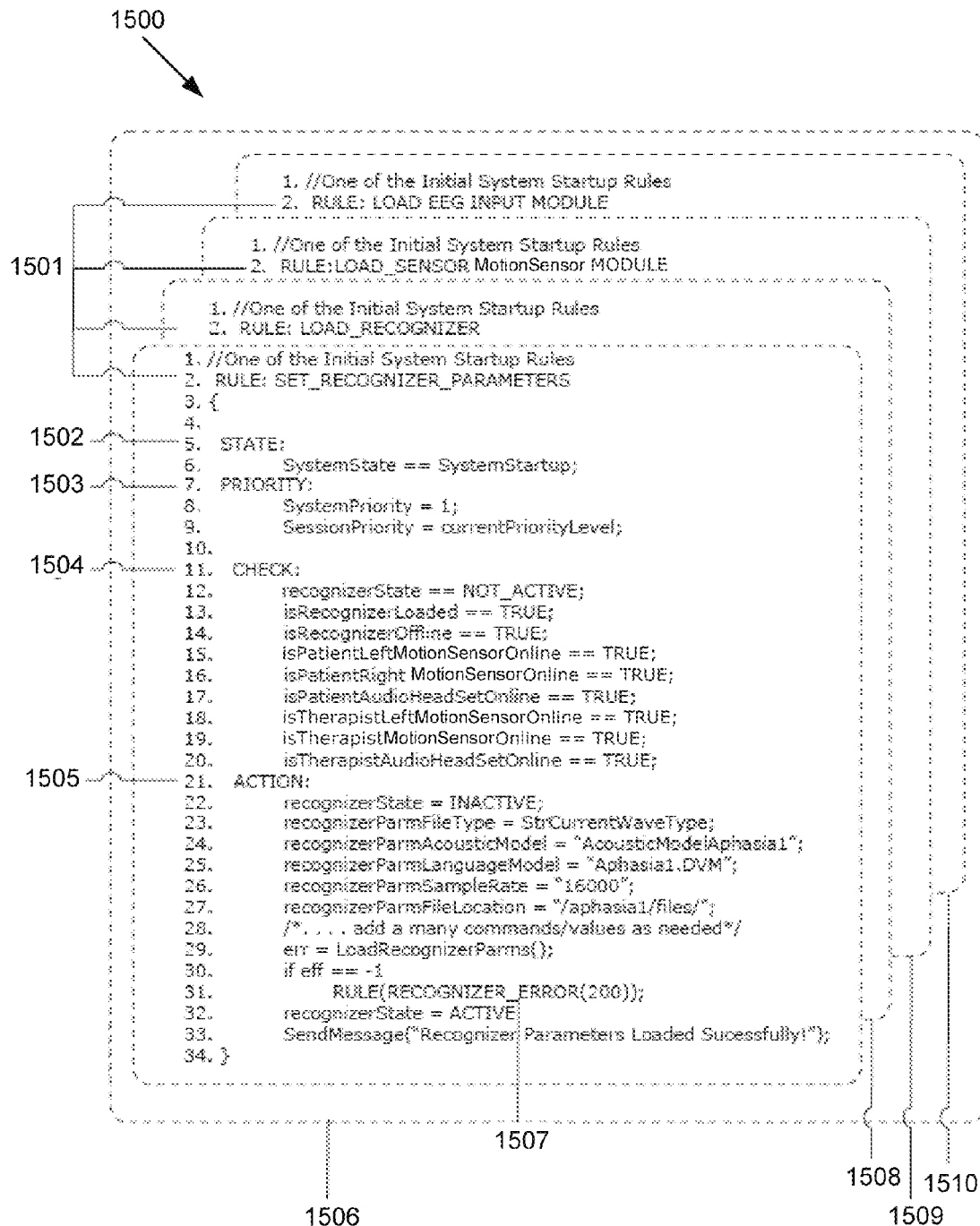
FIG. 15a is a schematic block diagram depicting one embodiment of a rules application for the startup and initialization phases input module in accordance with the present invention.

FIG. 15*a* is a schematic block diagram depicting one embodiment of a rules application 1500 for the startup and initialization phases input module in accordance with the present invention. As depicted, the rules application 1500 comprises instructions from the startup and initialization phase of the invention including rule action lines 1501, a state section 1502, a priority section 1503, a check section 1504, an action section 1505, a rule recognizer section 1507, a startup rule "load recognizer" 1508, a startup rule "load motion sensor module 1509, and a startup rule "load EEG input module" 1510.

As depicted, line 1 is a comment, here "//one of the initial system startup rules//" and is not processed by the inference engine. Line 2, 1501, contains the name of the rule. Lines 3 and 34 define the beginning and the end of the rule. The state section 1502 denotes the section of the rule at which state information can be added to the rule. Adding state information (line 6) enables rules to be categorized by specific state. This may allow the inference engine 1404 to bypass or include rules 1408, 1410 for processing based on the state of the system 200, 500 at the time of processing. The priority section 1503 processes priorities. Rules 1408 may be assigned a priority (line 8) and a session may also have a priority level. The priority section 1503 may be checked by the inference engine to give certain rules 1408 priority over other rules 1408. This may insure that processes requiring more critical evaluation receive the appropriate processing attention. The check section 1504 denotes the portion of the rule 1408 at which information is "checked" and where certain conditions must exist for the rule 1408 to complete or "fire". In the depicted embodiment, the recognizer state must be inactive (line 12), the recognizer must be loaded (line 13), the recognizer must be offline (line 14), the subject 202 and Session Guide 204 motion sensors must be functional and online (lines 15-16 & 18-19), the Session Guide 204 and subject 202 headsets must be on (lines 17 & 20). The action section 1505 commands appropriate action when a rule 1408 is activated, or "fired".

In the depicted embodiment line 29 reloads the recognizer parameters and lines 30 and 31 check to see if the parameters are loaded correctly. If there was an error line 29 the system 200, 500 loads a rule 1408 that handles the error (line 31). Otherwise the rule 1408 (generally) continues to fire at line 32 where the recognizer is placed in active mode again and line 33 sends a message that the recognizer parameters were successfully changed. This process of evaluating the rules 1408 continues through all active rules 1408 and the session is directed by the rules 1408 that are currently loaded and running in the system 200, 500. A session may have any number of rules 1408. The session may be terminated by either the session guide 204 or the system 200, 500 itself through a rule 1408 that meets the criteria to end the session.

The above referenced variables may be pre-defined by the system and are just a few of many that may be created to hold data and information about the session and the sampled deconstructed data. Additionally, variable names and values as defined in the rule above may be created and assigned at will by a person building a rule base 1402. In certain embodiments there is no fixed limit on the number of items that a rule 1408 may evaluate or compare.

Rules 1408, 1410 in a rule base 1402 define the knowledge of the system and are responsible for driving the system. In some embodiments the rule base 1402 comprises a knowledge base 514. Rules 1408, 1410 may be preprogrammed in the initial invention, and may also be added to the system 200, 500 by a system administrator or researcher as new knowledge becomes known. Rules 1408 allow the system 200, 500 to be trained and infused with reasoning knowledge, eliminating the need to redesign the system 200, 500 whenever new knowledge is added.

In certain embodiments the rule base 1402 design allows expert knowledge to be loaded into the system 200, 500 for use in making intelligent processing decisions as the system 200, 500 performs its functions and duties. Furthermore, in some embodiments rule base 1402 knowledge allows for the encapsulation and use of various amounts of expert knowledge that may exceed the capabilities and capacity of the human mind, and may be used to complete complex and intricate real-time decision making functions and tasks.

In some embodiments rules 1408 contain a specific syntax and form that allow the inference engine 1404 to process them and make intelligent decisions based on the output of the rules 1408 in the system 200, 500.

Rules may be divided into the following sections:
Priority/State Section
Check Section
Action Section
Conflict resolution.

Rules 1408 may have access to system 200, 500 variables that contain data information that has been collected and deconstructed by the system 200, 500 and its modules and rules 1408. Rules 1408 may read the values in the variables. In some embodiments rules 1408 can change the values of the variables. Rules may request the value for the variable be updated or populated from deconstructed data in the system 200, 500 memory. Any variable information that has been stored may be available to every rule 1408 in the system 200, 500. As a result, as one rule 1408 requests, adds, or modifies a variable all other rules 1408 may have access to the variables and their values and may accordingly inherit knowledge and data already learned from other rules 1408. Rules 1408 also have the ability to create their own variables and make them private or public to all rules 1408 in the system In various embodiments rules 1408 have the capability to perform logic and math functions in order to make intelligent decision about the data the rule 1408 has been created to for. Some of the logic capabilities of a rule 1408 are:
simple math (addition, subtraction, multiplication etc.)
complex math (log, sin, etc.)
logic comparison like less than, greater than, equal, less than or equal (i,e $<$, $>$, $<=$, $>=$, $==$, $!$ for not)

It is understood that this syntax and format is modifiable and customizable in the system 200, 500 design such that new rule 1408 logic and operators and variables may exist as standard programming features or may be added to and or deleted as the system 200, 500 learns about its environment and as space and needs may change.

In various embodiments rules have the ability to, but are not limited to: setting new data, adjusting existing data values or variables; creating, modifying, updating or deleting existing or new data variables; informing system components or modules to start, stop or modify tasks; setting new priorities, adjusting existing priorities; evaluating and processing data based on a weighting values, level of importance, certainty factors and fuzzy logic or values; eliciting input from users or internal or external modules or interfaces; controlling internal and external devices, processes, methods, calculations, timing, synchronization and CPU's and all other functions or components or methods or software algorithms that can be controlled or adjusted in the system 200, 500 or attached thereto; outputting information to users or internal or external modules or interfaces; create new rules or modify existing rules based on prior information; create, add, update delete state information; and create add, update, modify and delete knowledge variables of information.

In some embodiments the system is designed to accept rule bases 1402 that perform any type of intelligent reasoning process. The system 200, 500 is not limited to a fixed set of methods that are designed to perform finite specific and succinct set of tasks. Conversely, the system 200, 500 may be a facilitator of knowledge processing. Knowledge may be a dynamic component that is added to the system 200, 500 upon operation, allowing the system 200, 500 to perform a multiplicity of unique tasks.

In addition to being trainable by operators, the system 200, 500 may be capable of building its own rules 1408 or knowledge, based on current knowledge, data and newly identified trends. This may be accomplished by adding specially designed rule bases 1402 to the knowledge base module 514. In some embodiments the specially designed rule bases 1402 are capable of analyzing existing data, existing rule bases 1402 and system 200, 500 conditions. Based on this information, new rules 1408 may be designed to create additional new sets of rules 1408 that may be used in the system 200, 500, thus furthering functionality and enabling the system 200, 500 to become self-learning based on the experiences encountered.

FIG. 15b is a schematic block diagram illustrating one embodiment of a rules application action module 1512 in accordance with the present invention. As depicted, the rules application action module 1512 comprises an ask for patient response rule 1511, an activate speech recognition rule 1513, a get patient response rule 1514, and an analyze patient response rule 1515.

The sample rule application module 1512 here depicted to explain the basic operation of a rule comprises rules 1511, 1513, 1514 that may be used to set the parameters for the speech recognition recognizer in the system. The speech recognizer is the unit that recognizes what the patient says in response to a request. Rules 1511, 1513, 1514 may function on the basis of testing against certain known and requested knowledge and conditions.

Rules 1408 (in general) may be configured to imitate human mental processes in "thinking" and manage information when making reasoning decisions. A rule 1408 is said to be successful in its implementation if all the information the rule 1408 is testing for or requesting has been satisfied. In certain embodiments when all the information that it is testing for has been satisfied the rule 1408 passes (or fires). For example, a rule 1408 may carry out its intended functions or actions by calling the ask for patient response rule 1511, lines 18-21. Here a line may be set to a new variable. For example line 20 "have patient response" may be changed from "false" to another variable. A rule 1511 may reassign priority values to itself or other rules, or call another rule. For example, activation of the "ask for patient response" rule 1511, line 21 may call another rule 1513, "activate speech recognition". A rule 1513 may call an action (function/method) within the system that causes an action to be carried out, for example by calling the get patient response rule 1514 line 11 "send message".

If any part of the tests in the rule, for example 1511, fails then the entire rule 1511 fails and the inference engine moves on to the next rule to evaluate. For example if any of lines 4-7 (system state, priority, check) fail, then the entire rule 1511 would fail. All rules 1408 in the system 200, 500 are constantly evaluated and tested for pass-ability until a rule 1408 is found that passes. Once a rule 1408 passes it "fires" carries out its actions and then the inference engine 1404 continues processing the next rule 1408.

Note that rules 1511, 1513, 1514 can have different sections such as defined here for state (line 3), priority (line 5) check (line 7) that may also be used to determine if a rule passes or fails. These section heads can be added to rules 1511, 1513, 1514 as needed in order to apply different levels of granularity and separation between rules sets and state conditions in order to allow for more fluid and controlled knowledge sessions that can process information quickly and efficiently.

FIG. 15*c* is a schematic block diagram illustrating one embodiment of a rules conflict resolution module 1522 in accordance with the present invention. As depicted, the rules conflict resolution module 1522 comprises a set of conflict rules 1523, 1524, 1525, 1526, rule specific action lines 1516, 1517, a state section 1518, a priority section 1519, a check conflict section 1520, and a data variable 1521

For rule 1523 to pass, all the information in the state section 1518 (line 5), the priority section 1519 (line 7), and the check conflict section 1520 (line 11) must pass. If any of information or variable values in sections 1518, 1519, 1520 are false, then rule 1523 is bypassed and the inference engine 1404 moves on to considering and processing other rules 1408. If all items in sections 1518, 1519, 1520 pass then rule 1523 is set to fire mode and placed in a scheduler 1414 until all other rules 1408 that might also meet this criteria are found.

If multiple rules 1408 meet the criteria, the inference engine 1404 conflict manager 1416 makes decisions on which are the appropriate rules 1408 to fire. If no other rules 1408 meet the criteria, then the single rule 1423 "fires" and the action section 1505 commands its lines 22-33 to begin processing. Action section 1505 lines 22-27 set recognizer parameters and line 28 shows that unlimited actions may be added. In certain embodiments unlimited information can be added to the check conflict section 1520, priority section 1519 and state section 1518. In various embodiments sections of a rule 1408 may be added or created.

Figure 16:
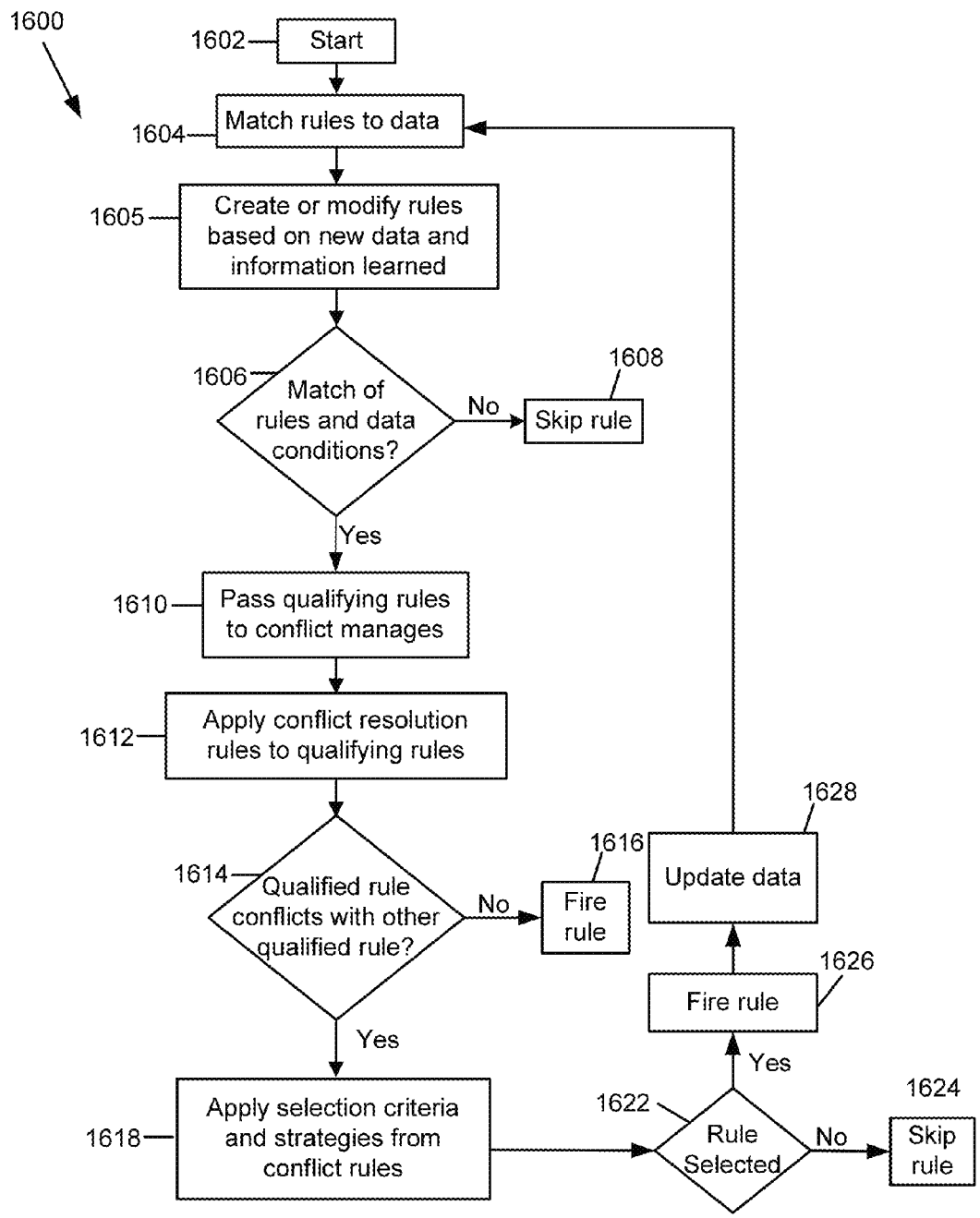
FIG. 16 is a schematic flow chart diagram depicting one embodiment of a method 1600 for rule selection and conflict resolution in accordance with the present invention.

FIG. 16 is a schematic flow chart diagram depicting one embodiment of a method 1600 for rule selection and conflict resolution in accordance with the present invention. In some embodiments of the method 1600 a start 1602 is followed by a first step 1604 that attempts to match all rules 116, 422, 1408 in the knowledge base module 512 that satisfy the current contents of the data store in the storage module 112. Rules may be created or modified based on new data and on information 1605 In certain embodiments a second step 1606 selects all the rules 116, 422, 1408 that meet the criteria for execution because all of the required data conditions exist for the rules 116, 422, 1408 to execute. Rules that do not match may be skipped, 1608.

In certain embodiments all the rules 116, 422, 1408 that are found to be candidates for execution (or firing) are then passed to the conflict manager module 528 for processing 1610. In such embodiments the conflict manager 528 applies 1612 the conflict resolution rules 1410 to the qualifying rules 116, 422, 1408 and makes decisions on which rules 116, 422, 1408 to fire/execute based on a variety of criteria that are stored in the rules 116, 422, 1408, 1410. In this step the inference engine 107, 1404 may apply selection criteria or strategies from the conflict rules 1410 to determine which functional rules 116, 422, 1408 are to be executed and which are not when conflicting rules 116, 422, 1408 are all candidates for execution.

A query 1614 determines which qualified rules 116, 422, 1408, if any, are in conflict with other qualified rules 116, 422, 1408. A rule 116, 422, 1408 that is not in conflict with other qualified rules 116, 422, 1408 may be fired 1616. Selection criteria 1618 are applied to qualified rules 116, 422, 1408 that are in conflict with other qualified rules 116, 422, 1408 and selection is determined 1622. Selected 1626 rules 116, 422, 1408 are fired 1626 and those not selected 1622 are skipped 1624. Data is updated 1628 and matched to rules 1604. Since the contents of the storage module 112 may be updated as rules 116, 422, 1408 are fired, a new set of rules 116, 422, 1410 will match during the next and each subsequent cycle after current rule actions are performed.

Figure 17A:
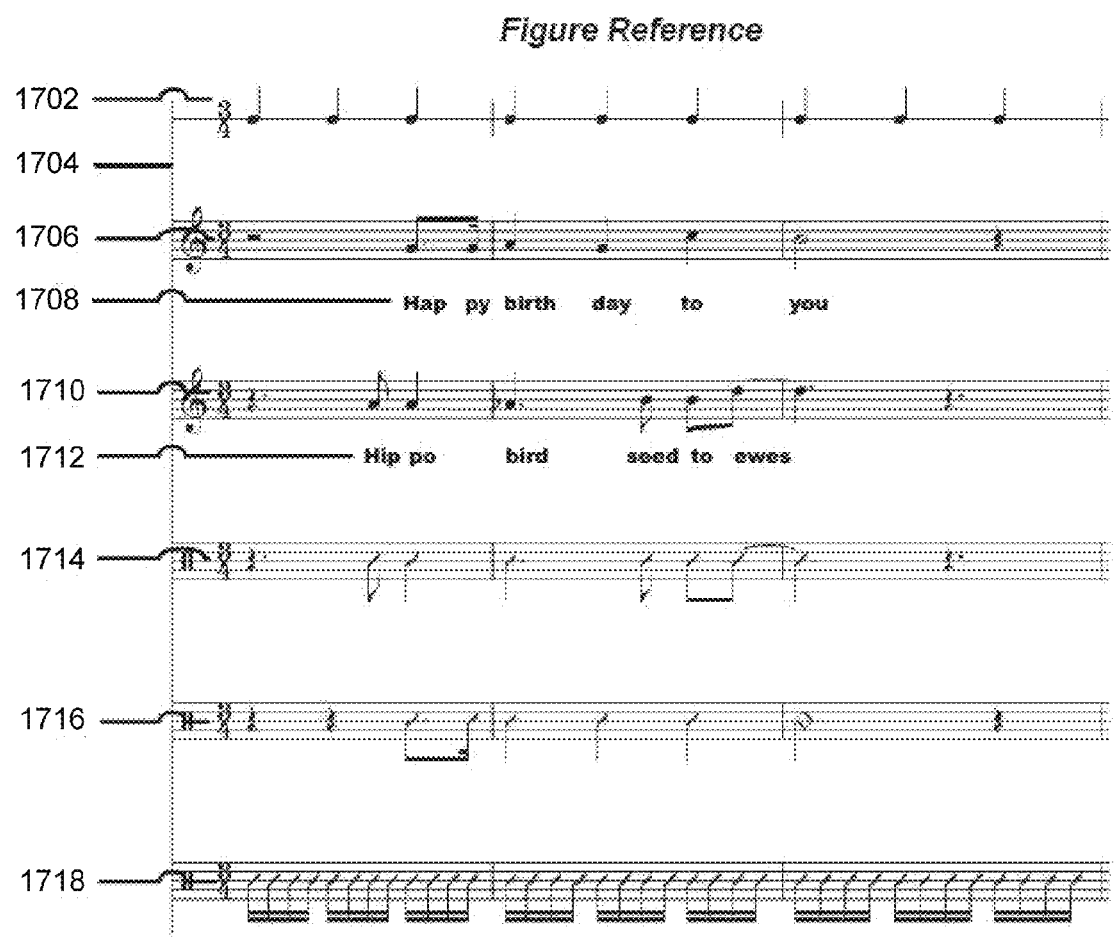
FIG. 17a depicts a basic musical score with words sung by both the system and the subject in response to a system request in accordance with the present invention.

FIG. 17*a* depicts a basic musical score 1700 with words sung by both the Session Guide 204 and the subject 202 in response to a system 200, 500 request in accordance with the present invention. As depicted, the basic musical score 1700 comprises a reference line 1 1702, a musical request 1706, a lyrics request 1708, a musical response 1710, a lyrics response 1712, a rhythm response 1714, a rhythm request 1716, and a beat reference line 1718.

The musical score 1700 depicts the Session Guide 204's melody 1706 and lyrics 1708 request. In this case the Session Guide 204, using his knowledge and the basic procedure of MIT makes an initial request to the subject 202 asking him to sing "Happy birthday to you" 1706, 1708. The Session Guide 204 demonstrates this request by singing "happy birthday to you" 1706, 1708 and at the same time taps out the rhythm on the patient's left hand. As depicted, the subject responds by singing "Hippo bird seed to ewes" 1710, 1712 where the words returned 1712 and the beats 1710 are off and out of sync with the actual song.

As a result of the subject 202's response the Session Guide 204 may request that the subject 202 sing the phrase again and the Session Guide 204 again sings and taps to the subject. The subject 202 responds with the same response only this time a little agitated and the rhythm varies slightly from the last time, but sometimes without significant improvement.

Figure 17B:
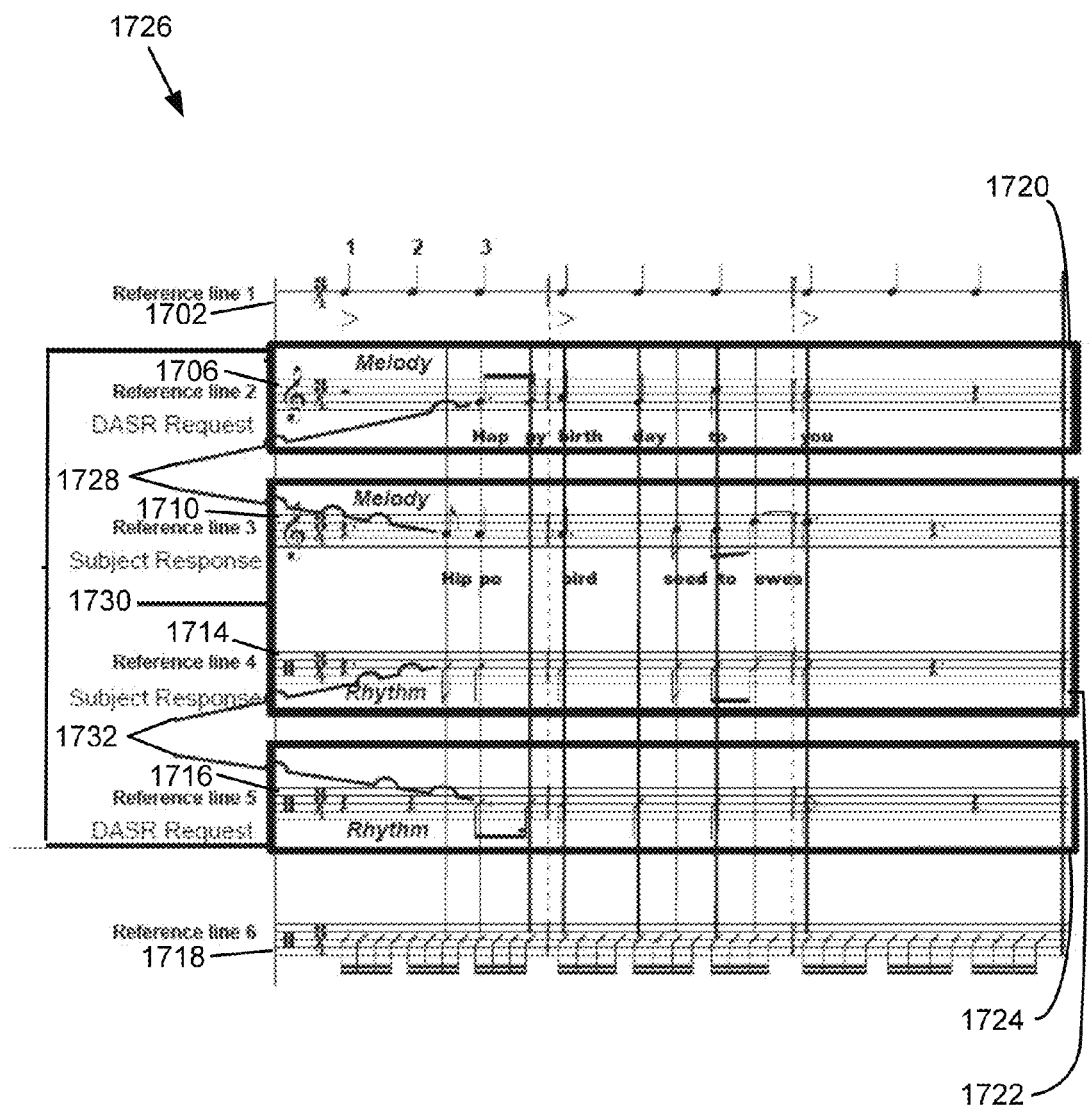
FIG. 17b further depicts one embodiment of a request response analysis with a musical note mismatch between the system request and the subject's response in accordance with the present invention.

FIG. 17*b* depicts one embodiment of a request response analysis 1726 with a musical note mismatch between the system 200, 500 action request and the subject 202's response accordance with the present invention. As depicted, the request response analysis 1726 comprises a reference line 1 1702, a musical request 1706, a lyrics request 1708, a musical response 1710, a lyrics response 1712, a rhythm response 1714, a rhythm request 1716, a beat reference line 1718, melody request 1720, a subject 202 response 1722, and a rhythm request 1724.

Here the subject 202's response 1722 begins one note off (G to A) from the request 1720 for melody, hits the third note correctly, but wanders off pitch for the rest of the line. The rhythm is also off in the subject 202 response 1722. Happy and Hippo are off by two beats. Birth and Bird are the same beat but off in duration and there are ongoing mismatches in the rest of the request.

Figure 17C:
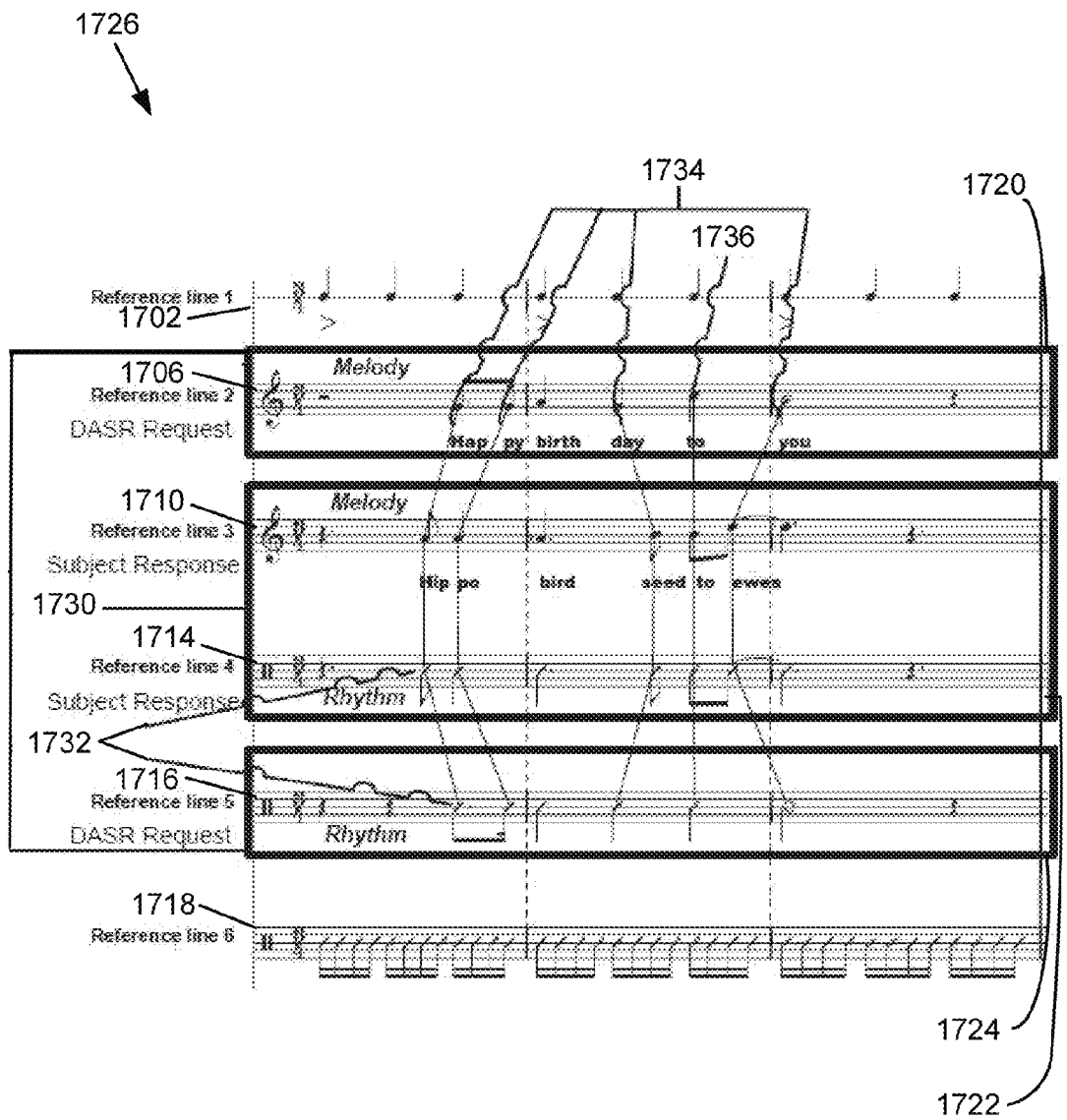
FIG. 17c depicts one embodiment of a request response analysis with a melody and rhythm mismatch between a system request and a subject's response in accordance with the present invention.

FIG. 17*c* depicts one embodiment of a further request response analysis 1726 with a melody and rhythm mismatch between the system 200, 500 request and the subject 202's response. As depicted, the response analysis 1726 comprises a reference line 1 1702, a musical request 1706, n lyrics request 1708, a musical response 1710, a lyrics response 1712, a rhythm response 1714, a rhythm request 1716, a beat reference line 1718, a mismatch 1732 between the request 1724, a request 1720 for rhythm, a response 1722 for rhythm, a request 1724 for rhythm, and lines 1734 and 1736 detailing the mismatch between the request 1720 and the subject 202 response 1722 for melody.

Figure 17D:
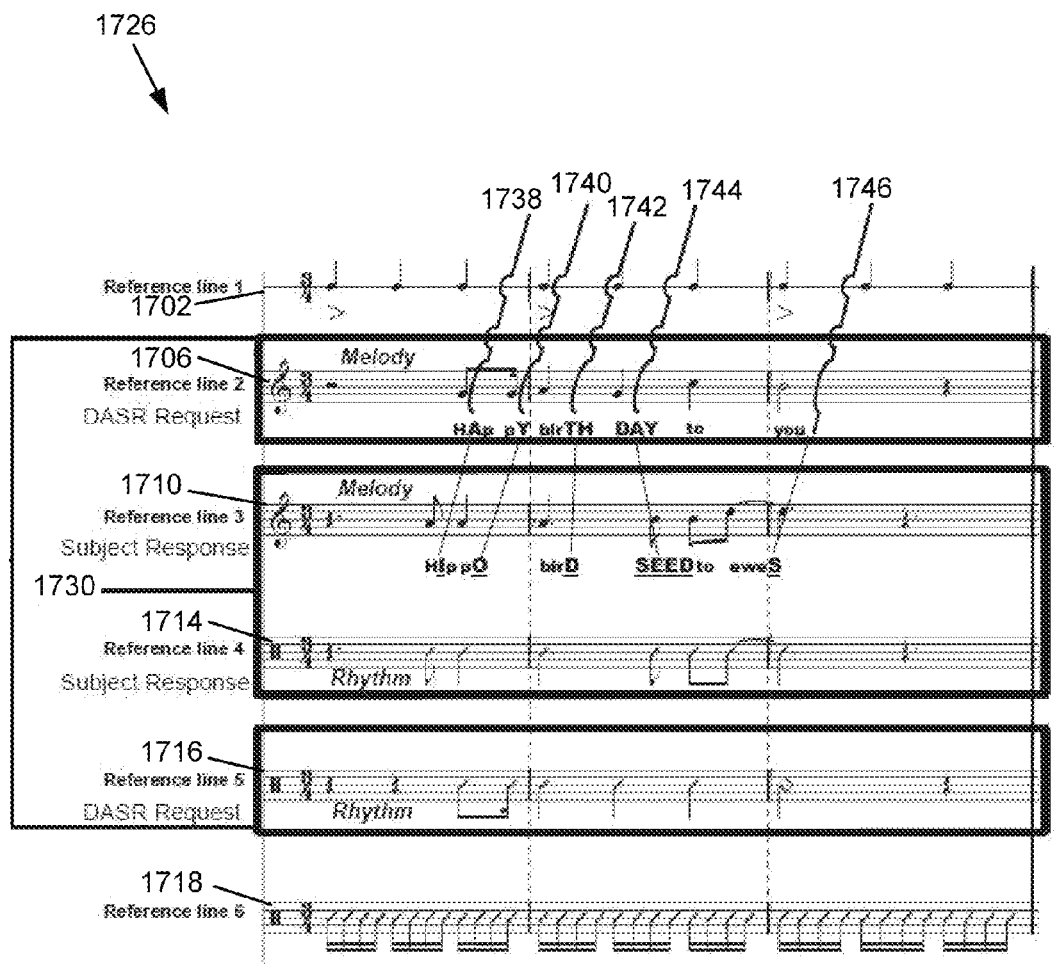
FIG. 17d depicts one embodiment of request response analyses with a lyrics mismatch between a system request and a subject's response in accordance with the present invention.

FIG. 17d depicts one embodiment of a request response analysis 726 with a lyrics mismatch between a system 200, 500 request and a subject 202's response accordance with the present invention. As depicted, the response analysis 1726 comprises a reference line 1 1702, a musical request 1706, a lyrics request 1708, a musical response 1710, a lyrics response 1712, a rhythm response 1714, a rhythm request 1716, a beat reference line 1718, a request 1720 for lyrics, a response 1722 for lyrics, a request 1724 for rhythm and a lyrics mismatch 1738, 1740, 1742, 1744, 1746 between the request 1720 and the response 1722.

The system 200, 500 using its inference engine 107 and rules 116, 422, 1408 has already correlated and grouped the requested and responded words accordingly:

Happy=Hippo
Birth=Bird
Day=Seed
To=To
You=Ewes

The word Happy and Hippo were close matches but the patient replaced 'i' for 'a' 870 and 'o' for 'y' 871 in Happy.

Figure 17E:
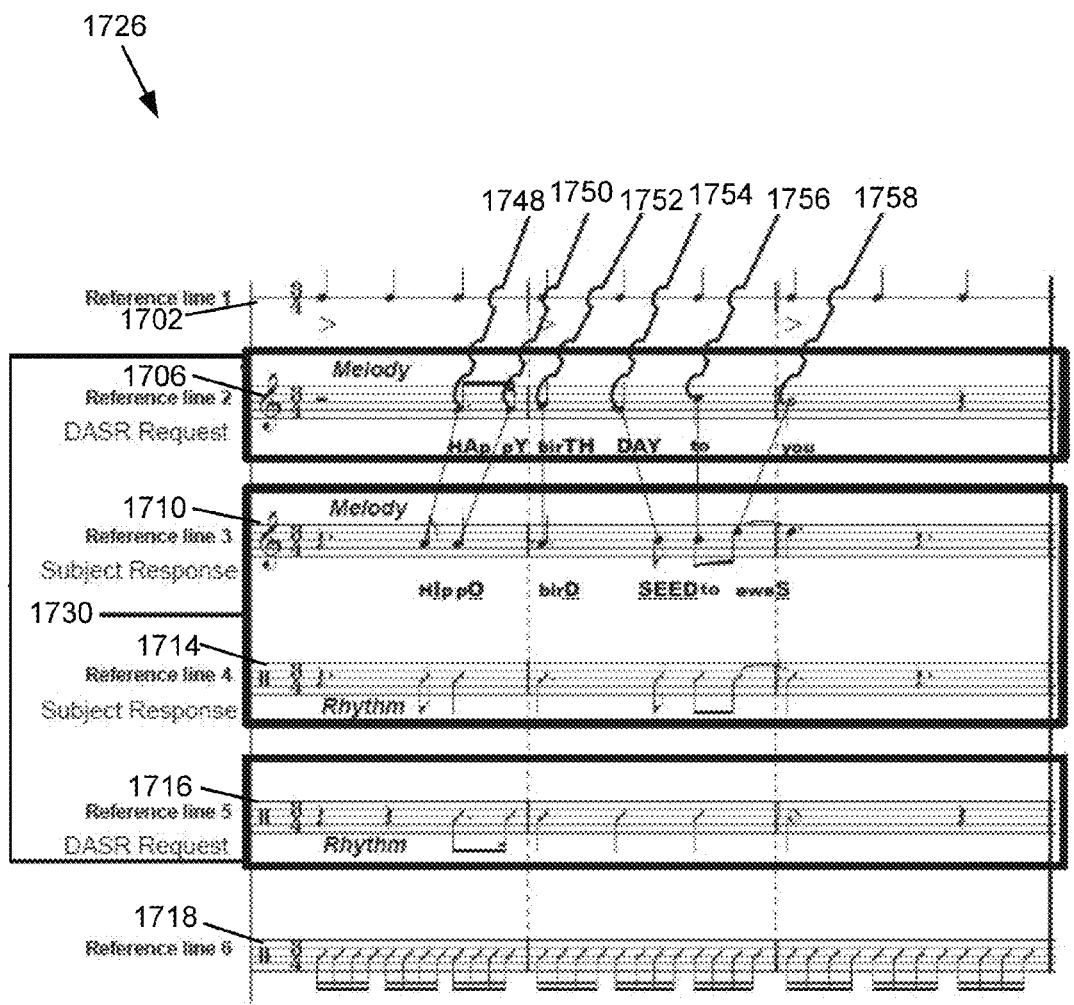
FIG. 17e depicts one embodiment of a request response analysis with a tempo/beat mismatch between a system request and a subject's response in accordance with the present invention.

FIG. 17e depicts one embodiment of request response analysis 1726 with a tempo/beat mismatch between a system 200, 500 request 1724 and the subject 202's response 1722 for tempo/beat. As depicted, the response analysis 1726 c As comprises a reference line 1 1702, a musical request 1706, a lyrics request 1708, a musical response 1710, a lyrics response 1712, a rhythm response 1714, a rhythm request 1716, a beat reference line 1718, a DASR melody request 1720, a subject response 1722, a rhythm request 1724, a reference line 3 1710, a reference line 4, 1714, a reference line 5 1716 a reference line 6, 1718, and the tempo/beat mismatch 1748, 1750, 1752, 1754, 1756, and 1758.

Based on the overall analysis of data for the entire prior patient response, as depicted in FIGS. 17a, 17b, 17c, 17d, and 173, the system 200, 500 formulates corrective actions. For example, the system 200, 500 may concentrate on getting the patient to sing the first word "Happy" only. Because the pitch was one note high on the patient response, the system 200, 500 may sing the word "Happy" one pitch lower in a new action request.

Based on prior history of other patients attempting to pronounce the word "Happy" the system 200, 500 may change the request from "Happy" (in which the patient failed to get the 'a' and 'y') to "Haypee". Because the rhythm was out of sync the system 200, 500 may change the rhythm based on past experience with rhythm.

A new modified action request may be made and this time the subject 202 may sing back "Happy" in the correct pitch and rhythm. The process continues on step by step as the system 200, 500 intelligently focuses and generates the request best configured to elicit an optimally improved response from the subject 202.

Figure 17F:
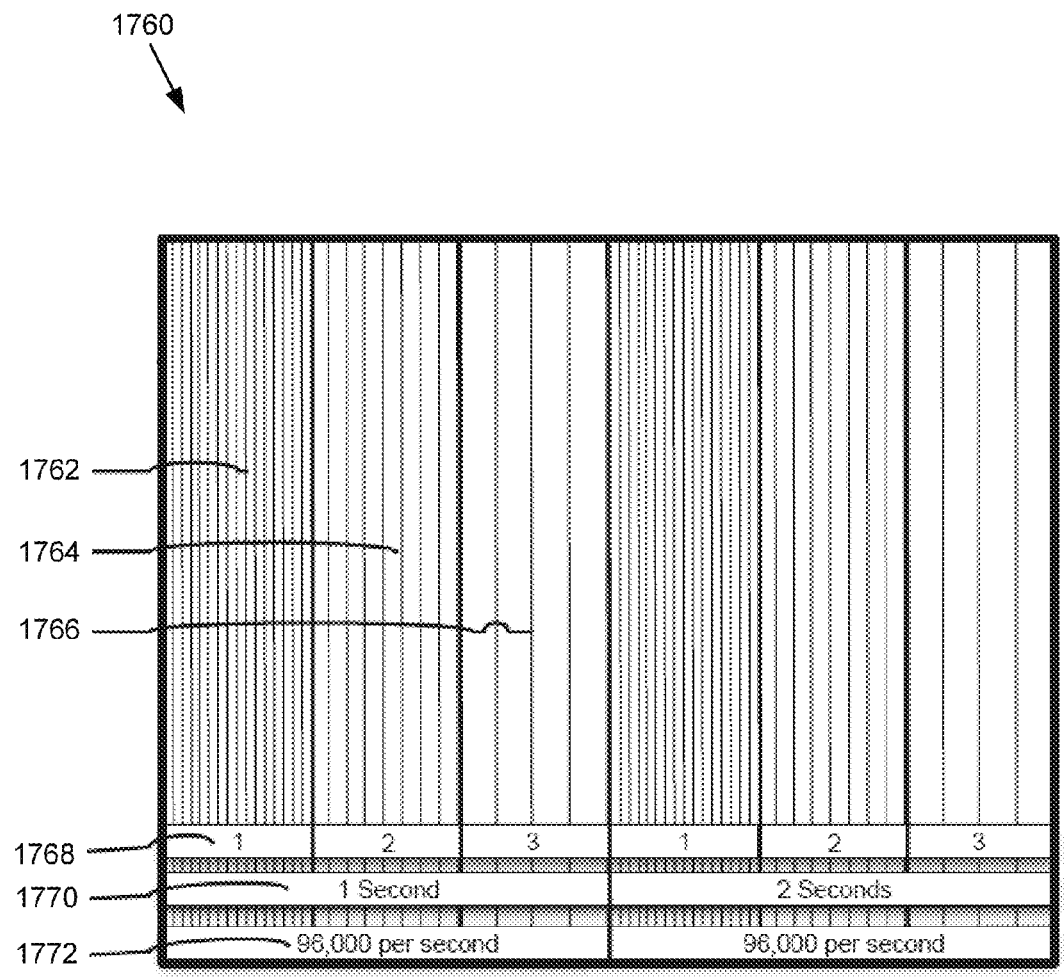
FIG. 17f is a line graph depicting time sampling in accordance with the present invention.

FIG. 17f is a line graph depicting time sampling 1760 at a default in accordance with the present invention. As depicted, the time sampling 1760 comprises sampling rates 1760, 1762, 1764 a rate panel indicator 1768, a sample duration indicator 1770, and a sampling rate indicator 1772.

In some embodiments data is captured and sampled as it is input into the system 200, 500. In various embodiments the sampling rate 1772 is 96000 samples per second 1762. Other sampling rates 1764 and 1766 may also be used, as may be appropriate for the type of data being captured. The sampling rate may be from 1 sample or less per second to 500,000 or more samples per second, including from 0 to 1, from 1 to 10, from 10 to 100, from 100 to 1000, from 1000 to 10,000, from 10,000 to 50,000, from 50,00 to 100,00, and from 100,000 to 500,000 or more samples per second.

Figure 18A:
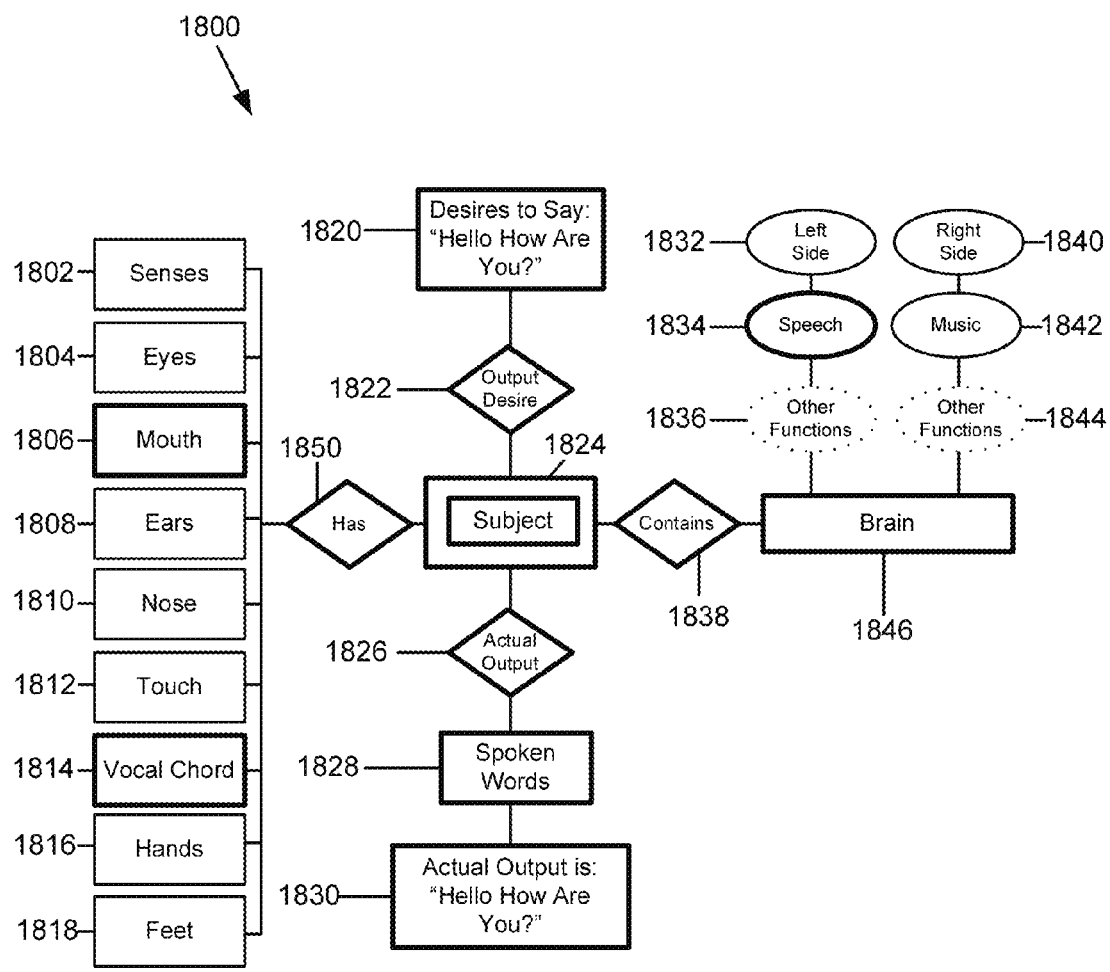
FIG. 18a is a schematic flow chart illustrating normal human structures and flow in a correct response to a system request in accordance with the present invention.

FIG. 18a is a schematic flow chart illustrating human structures and flow 1800 functioning normally in a correct response to a system request in accordance with the present invention. As depicted, the flow chart 1800 comprises senses 1802, eyes 1804, mouth 1806, ears 1808, nose 1810, touch 1812, vocal chord 1814, hands 1816, feet 1818, desired phrase 1820, output desire 1822, subject 1824, actual output 1826, spoken words 1828, word example 1830, cerebral connection 1838, brain 1846, left side 1832, speech center 1834, other functions 1836, right side 1840, music center 1842, other functions 1844 and a sensory connection 1850. In the depicted embodiment all of the physical structures are present and normal and the desired phrase 1820 is "Hello How are you?" The subject 1824 is able to activate the relevant speech center 1834 and mouth 1806 and vocal chords 1814 to execute the output desire 911 and speak the output phrase 1830.

Figure 18B:
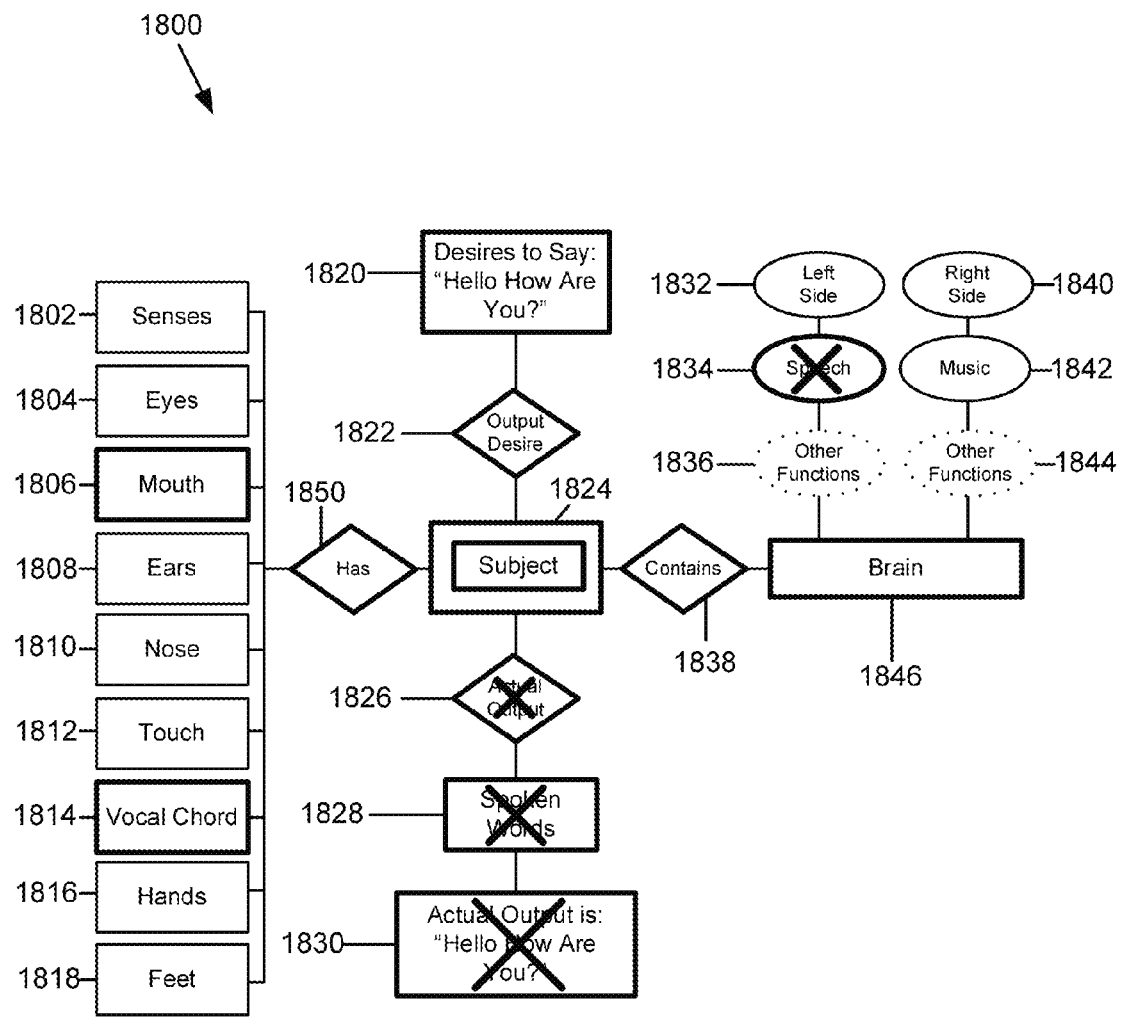
FIG. 18b is a schematic flow chart illustrating one embodiment of damaged human structures and interrupted flow in an aphasic subject.

FIG. 18b is a schematic flow chart illustrating one embodiment of human structures and flow 1800 as damaged and interrupted in an aphasic subject. As depicted the flow chart comprises senses 1802, eyes 1804, mouth 1806, ears 1808, nose 1810, touch 1812, vocal chord 1814, hands 1816, feet 1818, desired phrase 1820, output desire 1822, subject 1824, actual output 1826, spoken words 1828, word example 1830, cerebral connection 1838, brain 1846, left side 1832, speech center 1834, other functions 1836, right side 1840, music center 1842, other functions 1844, and a sensory connection 1850.

In this depiction the speech center 1834 is damaged and dysfunctional. Therefore, the patient cannot produce actual output 1826 of spoken words 1828 and say the desired phrase 1820.

Figure 18C:
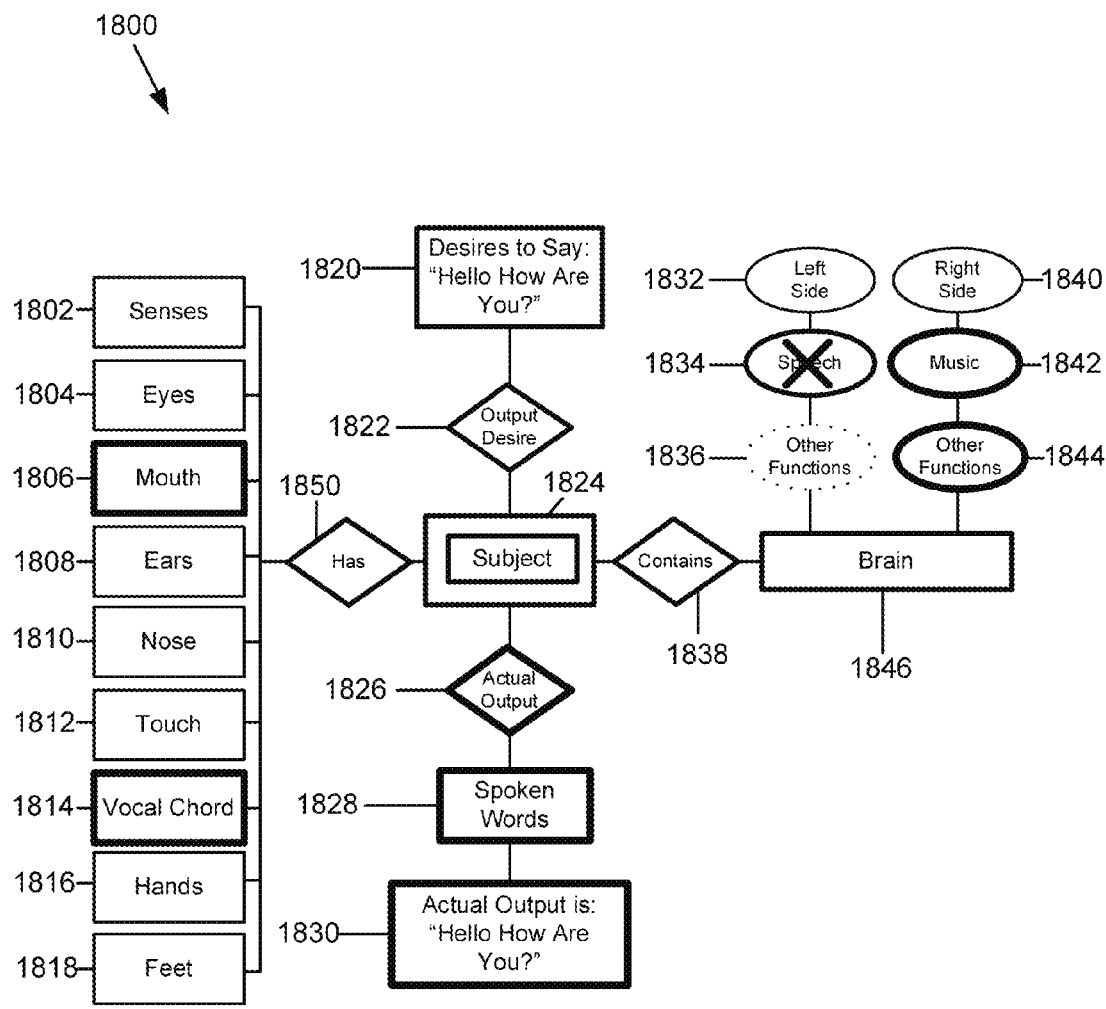
FIG. 18c is a schematic flow chart illustrating one embodiment of reconfigured human structures and flow in a post-therapy aphasic subject in accordance with the present invention.

FIG. 18c is a schematic flow chart illustrating one embodiment of human structures and flow 1800 as reconfigured in a post-therapy aphasic subject 1824 according to the present invention. As depicted the flow chart comprises senses 1802, eyes 1804, mouth 1806, ears 1908, nose 1810, touch 1812, vocal chord 1814, hands 1816, feet 1818, desired phrase 1820, output desire 1822, subject 1824, actual output 1826, spoken words 1828, word example 1830, cerebral connection 1838, brain 1846, left side 1832, speech center 1834, other functions 1836, right side 1840, music center 1842, other functions 1844, and a sensory connection 1850.

In this depiction the subject 1824 has learned to respond correctly to a system request through brain reconfiguration that recruits the music center 1842 and other functions 1844 to compensate for the damaged speech center 1834. The subject is therefore able to execute on the output desire 1822 and produce actual output 1826 of spoken words 1828 and say the desired phrase 1830 "Hello. How are you"?

From the foregoing, it is seen that the apparatus, system, and methods herein may provide enhanced capabilities for capturing data including for Aphasia patients. Additionally, the apparatus, system, and method may be integrated into computer and or software systems performing a variety of functions that could benefit from the acquisition, storage and intelligent reasoning components provided The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus configured to promote brain reconfiguration and at least one of speech enhancement, brain research, and brain damage diagnosis, the apparatus comprising:
    a data collection module configured to digitally collect action request response data from a human subject, the data comprising physiological data, and at least one of action data, and of sound data comprising at least one of speech data, music data, rhythm data, and other sound data;
    a physiological sensing device configured to sense physiological data indicating the subject's stress or satisfaction reaction to a request and to the subject's response and to sense the subject's brain function reaction to the request and to the subject's response;
    a data sample time slice software object comprising at least one of physiological data, sound data, rhythm data, music data, and action data, collected at a defined interval of less than about one minute and further comprising an object pointer uniquely corresponding to each class of data, and wherein all classes of incoming data are time synchronized so that incoming data is stored in the software object corresponding to the sampling time of the data and wherein the data density determines the stored sample density of each class of data with a NULL value inserted where a sample is absent for a class of data, wherein a property of the data sample time slice software object improves at least one of a speed, memory space, retrieval efficiency, and analysis capability of a relevant hardware and/or software of the apparatus;
    a real-time deconstruction hardware module configured to deconstruct the data into subcomponents expressed as a non-transitory digital signal in real time;
    an analysis module comprising an intelligent reasoning module configured to in real time digitally process and compare the request response digital signal subcomponents of the at least one of the action data and sound data with the matching subcomponents of the response request digital signal, correlate the subcomponents of the physiological response digital signal with at least one of the subcomponents of the subject's response digital signal to the action request and a baseline state, digitally associate the physiological subcomponents and other data subcomponents; and recommend a new action request configured to move the subject response toward a more accurate imitation of the action request and toward enhanced speech related brain function according to one or more learned rules, the one or more learned rules being derived as a function of one or more existing rules, new or existing data, and predefined conditions.

2. The apparatus of claim 1 wherein the analysis module is configured to apply machine logic and automated reasoning to the selection of the new action request.

3. The apparatus of claim 1 further comprising an import module configured to import external data optionally including from an specialized external hardware data monitoring device.

4. The apparatus of claim 1 wherein the physiological data comprises at least one of heartbeat, respiration rate, and galvanic skin response.

5. The apparatus of claim 1 further comprising at least one of a synchrotimer, a storage module, a process analyzer module, a data processing module, a data input capture module, a diagnostic module, a communication module, a testing module, a train module, a GUI, a brain reconfiguration evaluation module, and a user interface module.

6. The apparatus of claim 1 further comprising a reconstruction module configured to reconstruct at least one of original sound, rhythm, action, physiological, and other data.

7. The apparatus of claim 1 wherein the analysis module further comprises an inferencing engine configured to implement rules in the knowledge database according to specific conditions, the inferencing engine comprising at least one of:
    an interpreter configured to execute chosen functions or actions based on the application of corresponding base rules;
    a scheduler configured to maintain control over system plans and functionality; and
    a conflict manager configured to maintain consistency of decisions according to rule priorities.

8. The apparatus of claim 1 wherein the physiological data comprises at least one of brain reconfiguration data and other neurological data.

9. The apparatus of claim 8 wherein the brain reconfiguration data or other neurological data comprises at least one of EEG data, MRI data, fMRI data, and DTI data.

10. The apparatus of claim 8 wherein the brain reconfiguration data or other neurological data comprises indicia of at least one of elevated inter-hemispheric brain activity during action request response, the stimulation of the AF, and the growth of the AF.

11. The apparatus of claim 1 further comprising a knowledge module comprising at least one of an active data module, an internal memory module, a memory storage module, a session memory module, a rules module, a knowledge database, a rules database, and a rules priority module.

12. The apparatus of claim 11 wherein the knowledge module updates and self-modifies in real time based on at least one of new data and experience with the human subject.

13. The apparatus of claim 11 wherein the knowledge module updates and self-modifies in real time.

14. The apparatus of claim 11 wherein the knowledge module is self-learning and configured to accrue and link at least one of stored and incoming data to at least one of analysis and decision making.

15. The apparatus of claim 1 wherein the analysis module calculates a new response based on data and experience with at least one of a present human subject and previous subjects and on that basis generates a new request intelligently overcompensating for a response request error.

16. A system comprising:
    a therapeutic hardware apparatus configured to:
        supply to a subject an action to imitate wherein the action comprises at least one of action, speech, music, rhythm, and other sound, sense physiological data, action data, sound data, music data, speech data, rhythm data and melody data including pitch data in the subject's response,
transform the subject's response into a non-transitory digital signal, deconstruct the data digital signal into subcomponents, compare the subject's response to the original action, and supply a new action;
a database configured to store a library of actions and subject responses;
an incoming communication module configured to sense the subject's response and communicate said response to the therapeutic apparatus;
a data sample time slice software object comprising at least one of physiological data, sound data, rhythm data, music data, and action data collected at a defined interval of less than about one minute and further comprising an object pointer uniquely corresponding to each class of data, and wherein all classes of incoming data are time synchronized so that incoming data is stored in the software object corresponding to the sampling time of the data and wherein the data density determines the stored sample density of each class of data with a NULL value inserted where a sample is absent for a class of data, wherein a property of the data sample time slice software object improves at least one of a speed, memory space, retrieval efficiency, and analysis capability of a relevant hardware and/or software of the apparatus;
an outgoing communication module configured to communicate the new action to the subject;
specialized external data monitoring hardware;
an input device; and
at least one of an outside communication connection and an internal communication connection.

17. The system of claim 16 further comprising a reconstruction module configured to reconstruct at least one of original sound, rhythm, action, physiological, and other data.

18. The system of claim 16 wherein the specialized external data monitoring hardware is configured to measure at least one of heart rate, respiration rate, galvanic skin response, ECG, EGG, MRI fMRI and DTI.

19. The system of claim 16 further comprising communication protocols and at least one of a remote server platform and remote storage.

20. The system of claim 16 further comprising a computer readable storage medium storing a computer readable program code executed to perform operations for the system, the operations comprising:
supplying to a subject an action to imitate, wherein the action comprises at least one of speech, singing, melody, rhythm, other sound, and action;
sensing the subject response;
deconstructing the data into subcomponents;
transforming the subcomponents into a non-transitory digital signal comparing the subcomponents of the subject response to the subcomponents of the action request;
comparing the subcomponents of the subject physiological response to the subcomponents of at least one of the previous response or a baseline; and
recommending a new action configured to bring the subject response closer to the action request.

21. The operations of claim 20 further comprising applying the response data to an intelligent reasoning module configured to use acquired knowledge to formulate a next action request.

22. A method comprising:
supplying to at least one of a therapist and a subject an apparatus and specialized external data monitoring hardware, the apparatus configured to
provide the subject with an action request, wherein the action comprises at least one of speech, music, rhythm, other sound and action,
sense the subject response,
create a data sample time slice software object comprising at least one of physiological data, sound data, rhythm data, music data, and action data collected at a defined interval of less than about one minute and further comprising an object pointer uniquely corresponding to each class of data, and wherein all classes of incoming data are time synchronized so that incoming data is stored in the software object corresponding to the sampling time of the data and wherein the data density determines the stored sample density of each class of data with a NULL value inserted where a sample is absent for a class of data wherein a property of the data sample time slice software object improves at least one of a speed, memory space, retrieval efficiency, and analysis capability of a relevant hardware and/or software of the apparatus;
compare the subject response to the original action, and supply a new action request;
measuring the subject's physiological response to the action; and moderating the new action request to optimize the physiological response.

23. The method of claim 22 wherein the specialized external data monitoring hardware is configured to measure at least one of heart rate, respiration rate, galvanic skin response, ECG, EGG, MRI, fMRI, and DTI.

24. The method of claim 22 wherein the physiological response comprises at least one of a brain wave, AF growth, AF stimulation, brain changes, brain reconfiguration, and other neurological changes.

25. The apparatus of claim 1 wherein the defined, regular interval of the data collection is in the range of 0.01 samples per second to 100 samples per second, 100 samples per second to 1,000 samples per second, 1,000 samples per second to 10,000 samples per second, from 10,000 samples per second to 100,000 samples per second or from 100,000 samples per second to 1,000,000 samples per second or more.

26. The data sample time slice software object of claim 1 further comprising a deconstructed data sample subcomponent comprising one or more of motion sensor data, speech data, melody data, rhythm data, a rhythmic unit object pointer, a stress object pointer, a speed object pointer, a beat object pointer, a duration object pointer, a pulse object pointer, a time interval object pointer, a syncopation object pointer, an acceleration object pointer, a deceleration object pointer, a dynamics object pointer, a stress point object pointer, a first sample rate time slice class, a prior sample rate time slice class, a next sample rate time slice class, and a last sample rate time slice class.

27. The data sample time slice software object of claim 1 wherein the deconstructed data sample subcomponent is stored in a location pointed to by the relevant pointer.

28. The method of claim 24 further comprising providing a new action request of the type shown to trigger at least one of a desired physiological response and a desired neurological response.

29. The method of claim 28 wherein the physiological response comprises a cumulative brain or neurological response.

\* \* \* \* \*